(12) United States Patent
Gur et al.

(10) Patent No.: US 12,415,212 B2
(45) Date of Patent: Sep. 16, 2025

(54) INTEGRATED MEDICAL WASTE MANAGEMENT SYSTEM AND OPERATION

(71) Applicant: MAABAROT METAL WORKS LTD., Kibbutz Maabarot (IL)

(72) Inventors: Amit Gur, Kibbutz Maabarot (IL); Amit Sheleg, Kibbutz Maabarot (IL); Mark Gershkovich, Netanya (IL); Doron Egozi, Kibbutz Maabarot (IL)

(73) Assignee: MAABOROT METAL WORKS LTD., Kibbutz Maabarot (IL)

( * ) Notice: Subject to any disclaimer, the term of this patent is extended or adjusted under 35 U.S.C. 154(b) by 365 days.

(21) Appl. No.: 16/765,233

(22) PCT Filed: Nov. 19, 2018

(86) PCT No.: PCT/IL2018/051243
§ 371 (c)(1),
(2) Date: May 19, 2020

(87) PCT Pub. No.: WO2019/097520
PCT Pub. Date: May 23, 2019

(65) Prior Publication Data
US 2020/0290102 A1    Sep. 17, 2020

Related U.S. Application Data

(60) Provisional application No. 62/588,367, filed on Nov. 19, 2017.

(51) Int. Cl.
*B09B 3/00* (2022.01)
*A61L 2/10* (2006.01)
(Continued)

(52) U.S. Cl.
CPC .............. *B09B 3/0075* (2013.01); *A61L 2/10* (2013.01); *A61L 2/22* (2013.01); *A61L 11/00* (2013.01);
(Continued)

(58) Field of Classification Search
CPC .......... A61L 11/00; A61L 2/22; B02C 18/142; B02C 1/06
See application file for complete search history.

(56) References Cited

U.S. PATENT DOCUMENTS 5,185,126 A * 2/1993 Adamski ................... A61L 2/04
422/38
5,346,142 A * 9/1994 Miller ................... B09B 3/0075
241/606
(Continued)

FOREIGN PATENT DOCUMENTS

| CN | 107309044 A | * 11/2017 |
|---|---|---|
| CN | 107913896 A | 4/2018 |

(Continued)

OTHER PUBLICATIONS

CN 107309044 A Translation.*
(Continued)

*Primary Examiner* — Sean E Conley
*Assistant Examiner* — Changru Chen
(74) *Attorney, Agent, or Firm* — The Roy Gross Law Firm, LLC; Roy D. Gross

(57) ABSTRACT

A medical waste treatment system, comprising: (1) A main treatment unit comprising: a waste receiver cover comprising a UV lamp; a waste shredding unit comprising a shredding bin and at least two rotating shredding blades; a compression unit to push the medical waste towards the shredding blades; a separator to allow the passage of shredded medical waste of a predefined shape and diameter; and
(Continued)

a disinfectant delivery unit comprising a plurality of nozzles. (2) A disinfection unit which comprises a disinfectant mixing bin and a mixing unit. (3) A main liquid management unit comprising a disinfectant delivery unit that comprises a plurality of nozzles interconnected to the main treatment unit. (4) A separator unit to separate the liquid from shredded waste; and a centrifuge to further remove liquid from the shredded waste.

16 Claims, 20 Drawing Sheets

(51) Int. Cl.
    *A61L 2/22*     (2006.01)
    *A61L 11/00*     (2006.01)
    *B02C 1/00*     (2006.01)
    *B02C 18/14*     (2006.01)
    *B02C 19/00*     (2006.01)

(52) U.S. Cl.
    CPC ............. *B02C 1/00* (2013.01); *B02C 18/142* (2013.01); *B02C 19/0075* (2013.01); *A61L 2202/122* (2013.01); *A61L 2202/21* (2013.01); *B02C 2201/06* (2013.01)

(56) References Cited

U.S. PATENT DOCUMENTS

| | | | |
|---|---|---|---|
| 5,516,049 A * | 5/1996 | Zoncada | A61L 2/12 241/34 |
| 5,570,845 A * | 11/1996 | Lewis | B09B 3/0075 241/606 |
| 5,620,654 A | 4/1997 | Mosenson | |
| 5,799,883 A | 9/1998 | Lewis et al. | |
| 7,195,185 B2 | 3/2007 | Matlin | |
| 7,360,730 B2 | 4/2008 | Brown | |
| 7,748,654 B2 | 7/2010 | Brown | |
| 7,931,860 B1 * | 4/2011 | Lewis | A61L 2/07 422/26 |
| 8,282,892 B2 | 10/2012 | Sampson | |
| 8,318,086 B2 | 11/2012 | Chandrasekhar | |
| 8,318,104 B2 | 11/2012 | Lewis et al. | |
| 8,404,191 B2 | 3/2013 | Sampson | |
| 8,518,324 B2 | 8/2013 | Chandrasekhar | |
| 8,518,339 B1 * | 8/2013 | Jude | A61L 11/00 241/606 |
| 8,652,405 B2 | 2/2014 | Jude et al. | |
| 8,784,746 B2 | 7/2014 | Jude et al. | |
| 8,800,898 B2 | 8/2014 | Alford | |
| 9,393,569 B2 | 7/2016 | Morgan et al. | |
| 9,982,414 B2 | 5/2018 | Jang | |
| 2006/0014996 A1 * | 1/2006 | Brown | B02C 19/0075 588/249.5 |
| 2006/0091247 A1 * | 5/2006 | Matlin | B65F 1/067 241/36 |
| 2006/0288886 A1 * | 12/2006 | Schwelling | B02C 19/0081 100/98 R |
| 2008/0191071 A1 | 8/2008 | Brown | |
| 2009/0123339 A1 * | 5/2009 | Sampson | A61L 11/00 422/243 |
| 2010/0316526 A1 * | 12/2010 | Chandrasekhar | A61L 2/12 514/723 |
| 2011/0121112 A1 * | 5/2011 | Alford | B03B 9/06 241/24.1 |
| 2011/0165035 A1 | 7/2011 | Lewis et al. | |
| 2012/0328484 A1 | 12/2012 | Sampson | |
| 2013/0039812 A1 | 2/2013 | Chandrasekhar | |
| 2013/0041041 A1 | 2/2013 | Chandrasekhar | |
| 2013/0164177 A1 | 6/2013 | Sampson | |
| 2013/0175373 A1 | 7/2013 | Morgan et al. | |
| 2015/0034743 A1 | 2/2015 | Alford | |
| 2015/0139854 A1 | 5/2015 | Jude et al. | |
| 2017/0100498 A1 * | 4/2017 | Sobhy | A61L 2/22 |
| 2017/0328031 A1 * | 11/2017 | Jang | E02F 9/265 |
| 2018/0272395 A1 * | 9/2018 | Herriott | B09B 3/80 |

FOREIGN PATENT DOCUMENTS

| | | |
|---|---|---|
| EP | 0662346 A1 | 7/1995 |
| WO | 2009019570 A2 | 2/2009 |
| WO | 2019097520 A1 | 5/2019 |

OTHER PUBLICATIONS

International Search Report issued in PCT/IL2018/051243 dated Mar. 7, 2019.
International Preliminary Report of Patentability issued in PCT/IL2018/051243 dated Oct. 27, 2019.
Extended European Search Report, Jul. 29, 2021, Application No. 18877824.4, 7 Pages.

* cited by examiner

122

121

123

INTEGRATED MEDICAL WASTE MANAGEMENT SYSTEM AND OPERATION

CROSS-REFERENCE TO RELATED APPLICATIONS

The present application is the U.S. national phase of PCT Application PCT/IL2018/051243 filed on Nov. 19, 2018, which claims priority to U.S. Provisional Patent Application No. 62/588,367 dated Nov. 19, 2017, the disclosures of which are incorporated herein by reference in their entirety.

FIELD OF THE INVENTION

This invention relates generally to medical waste management and disposal and, in particular, to an integrated system with numerous improvements to encourage safe and proper operation.

BACKGROUND OF THE INVENTION

Medical waste, such as is generated in medical, veterinary, dental and laboratory facilities, includes a wide variety of materials and substances, such as bandages, gloves, infusion bags, hypodermic needles, syringes, products of dialysis, testing vials, plastic bags, tubes, containers, blood, and human and animal wastes. Medical waste must be disposed in a safe, expeditious and hazard-free manner. In large medical facilities, the medical waste is generally collected at a central location at hospital premises waiting to be evacuated by sub-contractor to be transported to a central or municipal special treatment center using incineration or steam disinfection before disposal into a landfill. Such processes are not only costly, but may also be environmentally unfriendly because of pollution generated during treatment, reliance upon transportation of the waste to an offsite treatment facility, and in less-than-optimal use of non-renewable resources.

Because of the different types of medical waste to be disposed of, a number of devices have been developed, which include shredders for shredding the medical waste in order to reduce the overall volume and to facilitate and improve disinfection.

The closest prior art is patent application US20130175373 ('373), which relates to an integrated medical waste management and treatment system that may include sensors, interlocks, communications links and/or other features for determining if the waste itself, the decontaminating disinfectant used in the process, and the status of the system are consistent with recommended or authorized system operation. System operation may be terminated if a condition inconsistent with recommended or authorized system operation is detected. Such compliance apparatus may include an electronic scale for determining the weight of the waste loaded into the receiver compartment, a metal detector, or a sensor for determining if the decontaminating disinfectant is a recommended or authorized disinfectant. A communications link may be provided for one or more of the systems to transmit information to a central station to deliver updates or commands associated with the recommended or authorized operation of each system.

Disadvantages found in patent application '373 include materials, such as medical waste containers, not properly feeding into the shredder, difficulties in ensuring that all the waste is properly disinfected, and a lack of safety features to protect a user against the internal machinery and against the exposure to pathogens during processing.

It is therefore a long felt need to provide a device which does not have difficulty in shredding certain types of materials, that does not have difficulty in adequately disinfecting all of the waste, and that does not lack sufficient safety measures.

SUMMARY OF THE INVENTION

It is the scope of the present invention to provide a medical waste treatment system (1000), comprising:
  a. a main treatment unit (100), said main treatment unit comprising:
    i. a waste receiver cover (110); and
    ii. a waste shredding unit (120), said waste shredding unit comprising a shredding bin (121) and at least two rotating shredding blades (124);
  b. a main liquid management unit (600) which comprises:
    i. a water/disinfectant mixing unit (604, 660), and
    ii. a first disinfectant delivery unit (605) interconnected to said main treatment unit (100);
  c. a separator unit (200) which comprises:
    i. a separator arm (202); and
    ii. an output chute (206); and
  d. a plurality of motor units (300) which comprises:
    i. a shredding motor unit (301) operative interconnected to said at least two rotating shredding blades (124);
    ii. a mixer motor unit (303) operative interconnected to said mixing unit (132); and
    iii. a separator unit motor;
wherein said first delivery unit (605) comprises a plurality of nozzles through which said disinfectant flows;
wherein said waste shredding unit (120) further comprises a second disinfectant delivery unit (607) comprising a plurality of nozzles through which said disinfectant flows;
further wherein said separation arm (202) further comprises a centrifuge (207) configured to further remove liquids from the shredded waste.

It is further a scope of the present invention to disclose the medical waste treatment system as disclosed above, wherein said waste receiver cover further comprises a window.

It is further a scope of the present invention to disclose the medical waste treatment system as disclosed above, wherein said main treatment unit (100) further comprises a disinfection unit (130) which comprises a disinfectant mixing bin (131) and a mixing unit (132);

It is further a scope of the present invention to disclose the medical waste treatment system as disclosed above, wherein said main liquid management unit (600) further comprises a liquid waste management unit (606). It is further a scope of the present invention to disclose the medical waste treatment system as disclosed above, wherein said separator arm (202) comprises a member of a group consisting of an elongated screw (201, 1202), a mechanical squeezer 1205, a centrifugal pump and any combination thereof.

It is further a scope of the present invention to disclose the medical waste treatment system as disclosed above, wherein said separator unit motor is selected from an elongated screw motor unit (304) operative interconnected to said long screw (201), and a mechanical squeezer motor and a centrifugal pump motor.

It is further a scope of the present invention to disclose the medical waste treatment system as disclosed above, wherein said waste receiver cover (110) further comprises a UV lamp configured to disinfect user's contact area.

It is further a scope of the present invention to disclose the medical waste treatment system as disclosed above, wherein said main treatment unit (100) further comprises a compression unit (122) operatively interconnected with a compressing motor unit (302), said compression unit is configured to push said medical waste towards said shredding blades (124).

It is further a scope of the present invention to disclose the medical waste treatment system as disclosed above, wherein said waste shredding unit (120) further comprises a first tray (126), said first tray comprising a plurality of orifices characterized by shape and diameter SD1, said shape and diameter configured to allow the passage of shredded medical waste in predefined particle shape and diameter.

It is further a scope of the present invention to disclose the medical waste treatment system as disclosed above, wherein said separator arm (202) further comprises a second tray (205), said second tray comprises a plurality of orifices characterized by shape and diameter SD2, said shape and diameter configured to allow the passage of liquids and block passage of solids of a predefined particle shape of diameter.

It is further a scope of the present invention to disclose the medical waste treatment system as disclosed above, wherein said waste shredding unit (120) further comprises a grating 126 configured to allow the passage of shredded medical waste in predefined particle shape and diameter.

It is further a scope of the present invention to disclose the medical waste treatment system as disclosed above, further comprising an electrical unit (400).

It is further a scope of the present invention to disclose the medical waste treatment system as disclosed above further comprising an operator panel unit (500).

It is further a scope of the present invention to disclose the medical waste treatment system as disclosed above, wherein said waste receiver cover further comprises a safety mechanism configured to prevent operation of said system unless said waste receiver cover is closed.

It is further a scope of the present invention to disclose the medical waste treatment system as disclosed above, wherein said compression unit is characterized by a plurality of closing arms.

It is further a scope of the present invention to disclose the medical waste treatment system as disclosed above, wherein said compression unit is characterized by a pressing plate.

It is further a scope of the present invention to disclose the medical waste treatment system as disclosed above, wherein said SD1 is characterized by any geometrical shape and a diameter from about 16 millimeters to about 22 millimeters.

It is further a scope of the present invention to disclose the medical waste treatment system as disclosed above, wherein at least one of said at least two rotating shredding blades is configured to rotate at different velocity from at least one other of said at least two rotating shredding blades.

It is further a scope of the present invention to disclose the medical waste treatment system as disclosed above, wherein said SD2 is characterized by any geometrical shape and a diameter from about 1 millimeter to about 10 millimeters.

It is further a scope of the present invention to disclose the medical waste treatment system as disclosed above, wherein said first tray and said second tray are configured to be easily replaceable by the user.

It is further a scope of the present invention to disclose the medical waste treatment system as disclosed above, wherein said chemical disinfectant management unit (606) comprises an exit valve configured to manage the evacuation rate of the liquids exiting said disinfectant mixing bin (131) thereby controlling the amount of waste entering said long screw (201).

It is further a scope of the present invention to disclose the medical waste treatment system as disclosed above, wherein said long screw (201) is configured to rotate at different velocities It is further a scope of the present invention to disclose the medical waste treatment system as disclosed above, wherein said a centrifuge (207) further comprises a UV lamp.

It is further a scope of the present invention to disclose the medical waste treatment system as disclosed above, wherein said electrical unit (400) comprises a Variable Speed Drive (VSD) (403).

It is further a scope of the present invention to disclose the medical waste treatment system as disclosed above, wherein said operator panel unit (500) comprises an emergency stop button in case of emergencies.

It is further a scope of the present invention to disclose the medical waste treatment system as disclosed above, wherein said water/disinfectant mixing unit (604) is configured to mix between the incoming water and the disinfectant concentrate by means of creating vortex forces of said water in the delivery tubes thereby forcing the mixing of said disinfectant concentrate and said water.

It is further a scope of the present invention to disclose the medical waste treatment system as disclosed above, wherein said system further comprises a plurality of sensors operatively interconnected to different parts of the system.

It is further a scope of the present invention to disclose the medical waste treatment system as disclosed above, wherein a sensor is selected from a group consisting of:
  a. a waste receiver cover sensor configured to monitor if the said cover has been properly closed;
  b. a compressing unit sensor configured to detect resistance and evaluate quantity of said waste in said waste shredding unit (120);
  c. rotating shredding blades sensors configured to monitor the current of said shredding motor unit (301);
  d. first and second tray sensors configured to monitor the correct positioning of said trays (126, 205);
  e. disinfection unit sensor configured to monitor the quantity of each of the content inside said disinfectant mixing bin (131):
  f. long screw sensor configured to monitor real-time performance information of the rotational operation of said long screw (201);
  g. disinfectant RFID sensor configured to monitor the actual container of disinfectant being used;
  h. at least one temperature sensor;
  i. at least one flow meter and at least one pressure gauge;
  j. at least one load cell; and
  k. any combination thereof.

It is further a scope of the present invention to disclose the medical waste treatment system as disclosed above, wherein said disinfectant is characterized by:
  a. having a broad microbiological efficacy;
  b. having a low application concentration;
  c. having high efficiency rates at low application temperatures;
  d. having easy rinsing properties; and
  e. being ecologically friendly.

It is further a scope of the present invention to disclose the medical waste treatment system as disclosed above, wherein the system further comprises communication means configured to connect to external sources.

It is further a scope of the present invention to disclose the medical waste treatment system as disclosed above, wherein said external sources are selected from a group consisting of: a cloud based server; a cellphone; a tablet; any combination thereof.

It is further a scope of the present invention to disclose the medical waste treatment system as disclosed above, wherein said cloud based server is configured to: monitor technical performance, operational efficiencies, chemical allowance and exact usage according to exact specifications; the monitoring parameters are selectively available to the user, a technician, an owner, a distributer and regulatory bodies.

It is further a scope of the present invention to disclose a method to treat medical waste, comprising steps of:
a. providing a medical waste treatment system comprising:
   i. a main treatment unit (100), said main treatment unit comprising:
      1. a waste receiver cover (110); and
      2. a waste shredding unit (120), said waste shredding unit comprising a shredding bin (121) and at least two rotating shredding blades (124);
   ii. a main liquid/chemical management unit (600) which comprises:
      1. a water/disinfectant mixing unit (604, 660), and
      2. a first disinfectant delivery unit (605) interconnected to said main treatment unit (100);
   iii. a separator unit (200) which comprises:
      1. a separator arm (202); and
      2. an output chute (206); and
   iv. a plurality of motor units (300) which comprises:
      1. a shredding motor unit (301) operative interconnected to said at least two rotating shredding blades (124);
      2. a mixer motor unit (303) operative interconnected to said mixing unit (132); and
      3. a separator unit motor;
b. manually pressing a start button;
c. manually opening said waste receiver cover (110);
d. manually placing waste in said waste shredding unit (120);
e. manually closing said waste receiver cover (120);
f. automatically performing a shredding and disinfecting protocol, comprising steps of:
   i. concomitantly activating the disinfectant/water mixing unit of lower sprayer nozzle 813 and the rotating shredding blades 815;
   ii. assessing if a minimum quantity of disinfectant has been provided 819;
   iii. activating a mixer in the mixing unit 821;
   iv. quantifying the amount of shredded waste coming out the shredder and providing sufficient disinfectant according to the predetermined ratio of shredded waste/disinfectant 822;
   v. checking if all the disinfectant required has been provided 823;
   vi. checking if the mixing bin is at optimal capacity 825;
   vii. if yes, stopping said rotating shredding blades;
   viii. activating the mixer for a predetermined period of time 827.
   ix. opening the exit valve of the waste management system 828 and activating the separation arm;
   x. checking if the mixing bin is empty 830.
   xi. continuing operation of the separation arm for a predetermined period of time 832 to allow a remainder of said waste to exit the separation arm; and
   xii. stopping the separation arm 833.

wherein said method further comprises a step of disinfecting said waste receiver cover and said waste shredding unit, performed after said step (b);
wherein said method further comprises a step of activating the compression unit after said step (i);
wherein said method further comprises a step of activating the centrifuge at the end of the separation arm for a predetermined period of time after step (ix).

It is further a scope of the present invention to disclose the method as disclosed above, wherein said predetermined ratio of shredded waste / disinfectant is from about 1:1 to about 1:3.

It is further a scope of the present invention to disclose the method as disclosed above, wherein said optimal capacity depends on a size of the mixing bin.

It is further a scope of the present invention to disclose the method as disclosed above, wherein any of said predetermined periods of time is in a range from about 1 minute to about 60 minutes.

DETAILED DESCRIPTION OF THE INVENTION

The terms "formula", "liquid" and "disinfectant liquid" will hereinafter refer synonymously to a mixture of water and disinfectant.

The term "disinfectant concentrate" will hereinafter refer to concentrated disinfectant, before admixture with water.

The term "disinfectant" will hereinafter refer to the chemical mixture comprising the disinfectant material.

The term "about" will hereinafter refer to a range of plus or minus 10% around a stated value.

FIGS. 1-9 illustrate an embodiment of a bio-medical waste (B. M. W.) disinfecting shredder system, while FIGS.

10-15 illustrate an embodiment of the B. M. W. disinfecting shredder system with modifications configured to increase the flexibility and effectiveness of the system.

Figure 1A:
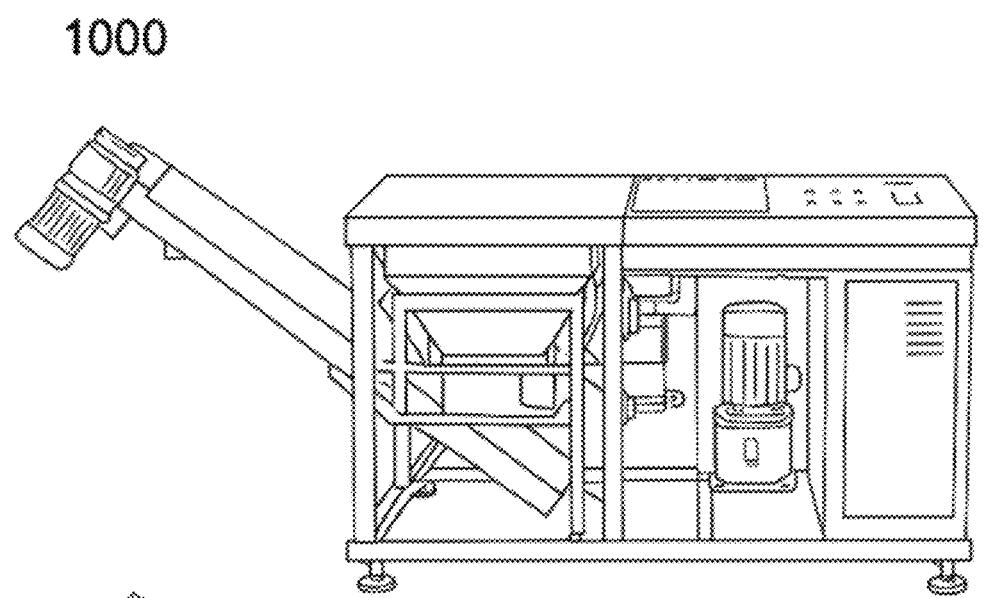
FIGS. 1A-1B illustrate a medical waste treatment and disposal system according to the present invention.

Fig. 1a illustrates an embodiment of a B. M. W. disinfecting shredder system 1000 to which the inventions disclosed herein are applicable, with the understanding that some or all of the various improvements and modifications are applicable to other medical waste systems, including those described in the Background section, above. Moreover, the various improvements and modifications are patently distinct in the sense that they may be used individually or in any combination thereof for improved performance, reporting, maintenance, safety or other operational characteristics.

Figure 1B:
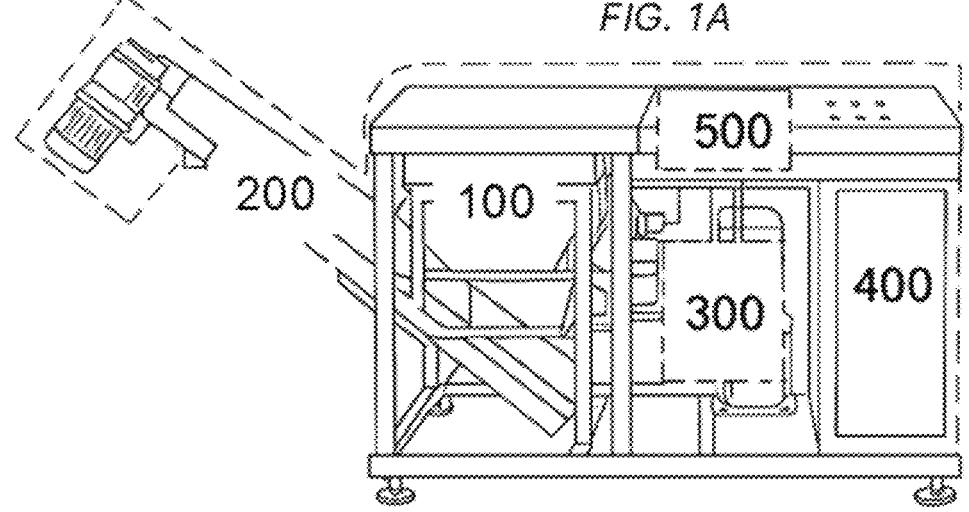

In order to simplify the explanation of the medical waste treatment and disposal system 1000, the system, as disclosed in FIG. 1*b*, illustrates the system's 5 main units, including: a main treatment unit 100 to receive the medical waste, and shred and decontaminate it. A separator unit 200 which separates the solid waste from formula (water plus disinfectant), removes the used formula to the sewage and transfers the treated waste into an ordinary garbage container (not shown) for removal. A variety of motor units 300 provide the different units with all power required for their performance An electrical unit 400. An operator panel unit 500. And a main liquid management unit 600.

The different units will be now described.

Figure 2:
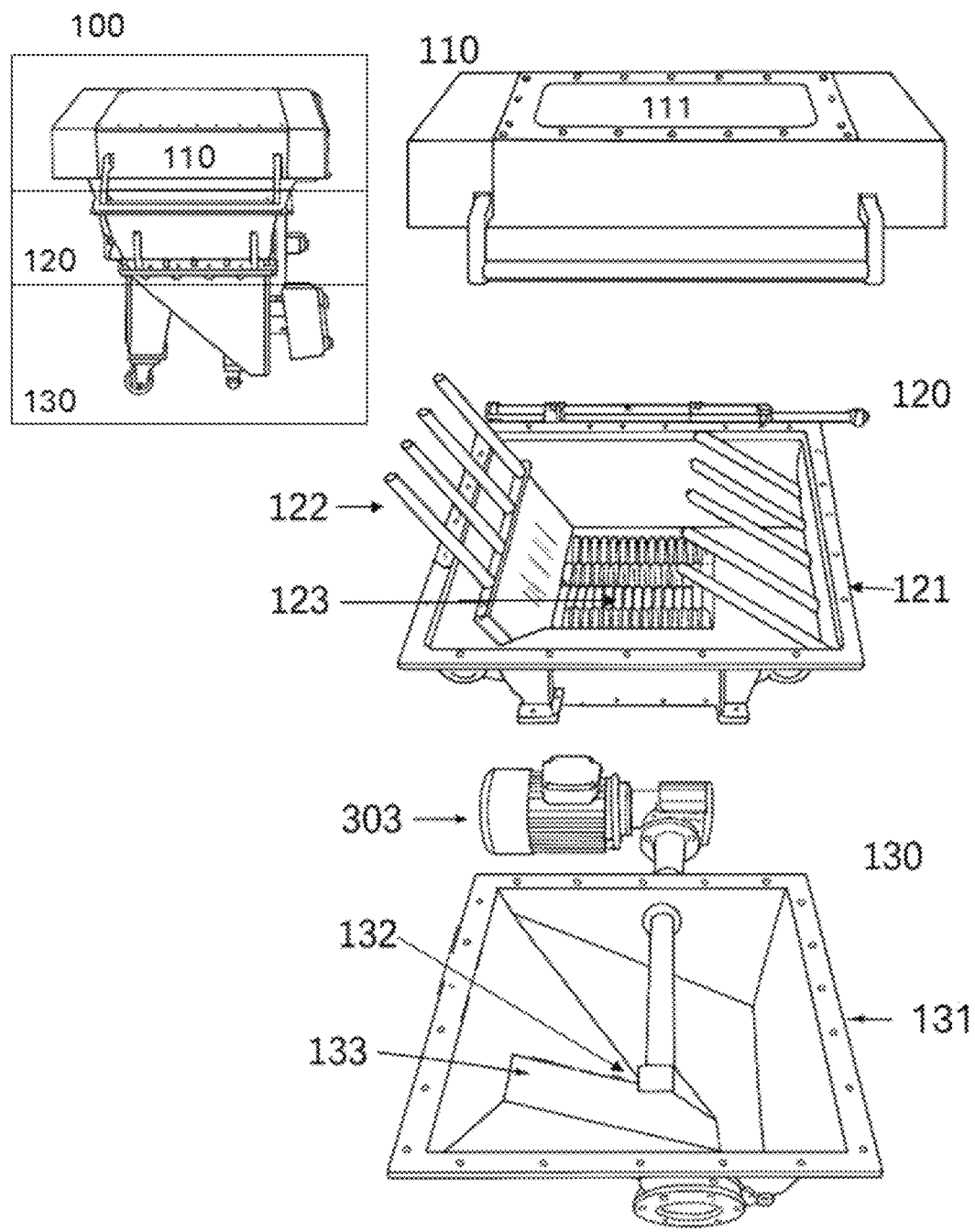
FIG. 2 shows an isolated view of the main treatment unit 100.

FIG. 2 shows an isolated view of the main treatment unit 100. The main treatment unit 100 can be divided into 3 parts: the waste receiver cover 110, the waste shredding unit 120 comprising a shredder 123 and a disinfection unit 130. The waste receiver cover 110 is manually opened to introduce the waste. The waste receiver cover 110 comprises at least one mechanism that prevents operation of the system until waste receiver cover 110 has been properly closed. Furthermore, the waste receiver cover 110 comprises a UV lamp, which is activated during the cycle and for a period of time after every cycle. These features are important for the safety of the user and also increase disinfection of the waste. The waste receiver cover may also comprise a window 111, through which a user may assess if all the waste has been shredded, look for problems and more. Waste is introduced into the waste shredding unit 120 via the open waste receiver cover 110. The waste shredding unit 120 comprises a shredding bin 121 where the waste is accumulated before it is shredded, a compression unit 122, in the embodiment shown, in the form of closing arms, which push the waste downwards toward the rotating shredding blades 124, and finally, the rotating shredding blades 124. In some embodiments, instead of closing arms, the machine comprises a pressing plate located on the lower side of the waste receiver cover 110. The pressing plate, when activated, moves vertically downward, pushing the waste into the rotating shredding blades 124. The compression unit 122 helps reduce shredding time significantly, in comparison to prior art systems. As the waste is shredded, it falls into the disinfection unit 130. The disinfection unit 130 comprises a disinfectant mixing bin 131, a mixing unit 132, in the embodiment shown, in the form of a propeller connected to a dedicated motor 303, and a disinfectant delivery system (not shown, see below). The open passage 133 of the separator unit 200 connects the separator unit 200 to the lower part 203 of the separation arm 202, (not shown). The mixing unit 132 enables a more aggressive and more effective disinfection of the waste. In some embodiments, the propeller further shreds the waste. In some embodiments, the disinfection unit 130 further comprises a window that allows the user to monitor the disinfectant liquid exiting the nozzles and the mixing of the waste with the disinfectant liquid.

Figure 3A:
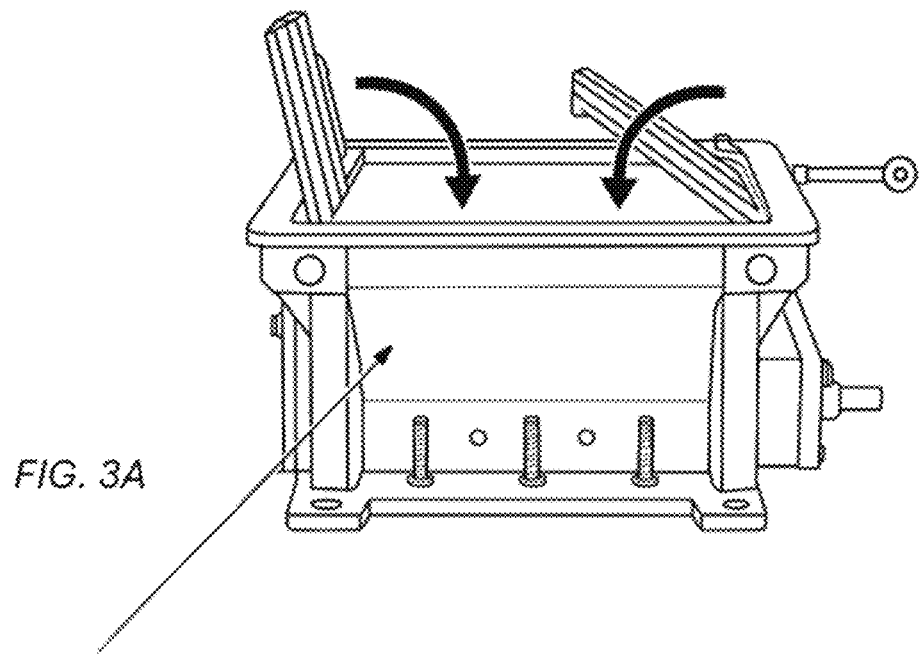
FIGS. 3A-3B show the mechanisms of action of two embodiments of the compression unit 122.
Figure 3B:
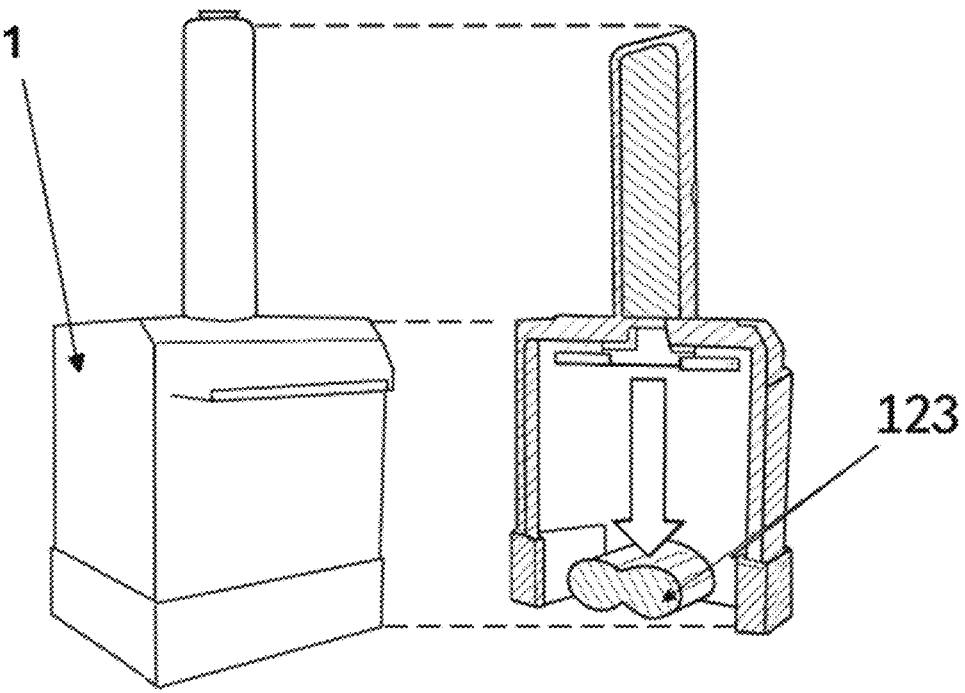

FIG. 3A-B shows the mechanism of action of two embodiments of the compression unit 122. In FIG. 3A, an embodiment with closing arms is disclosed. Each of the plurality of arms is rotatably attached to a wall of the shredding bin, preferably with at least one arm on each of two opposite sides of the shredding bin. The arms rotate downwardly, as shown by the black arrows. In this way, the waste is pushed downward towards the rotating shredding blades 124. FIG. 3B shows, a schematic embodiment, not in scale, of a compression unit comprising a pressing plate. As disclosed above, the pressing plate moves vertically downward (white arrow), pushing the waste into the rotating shredding blades 124.

Figure 4:
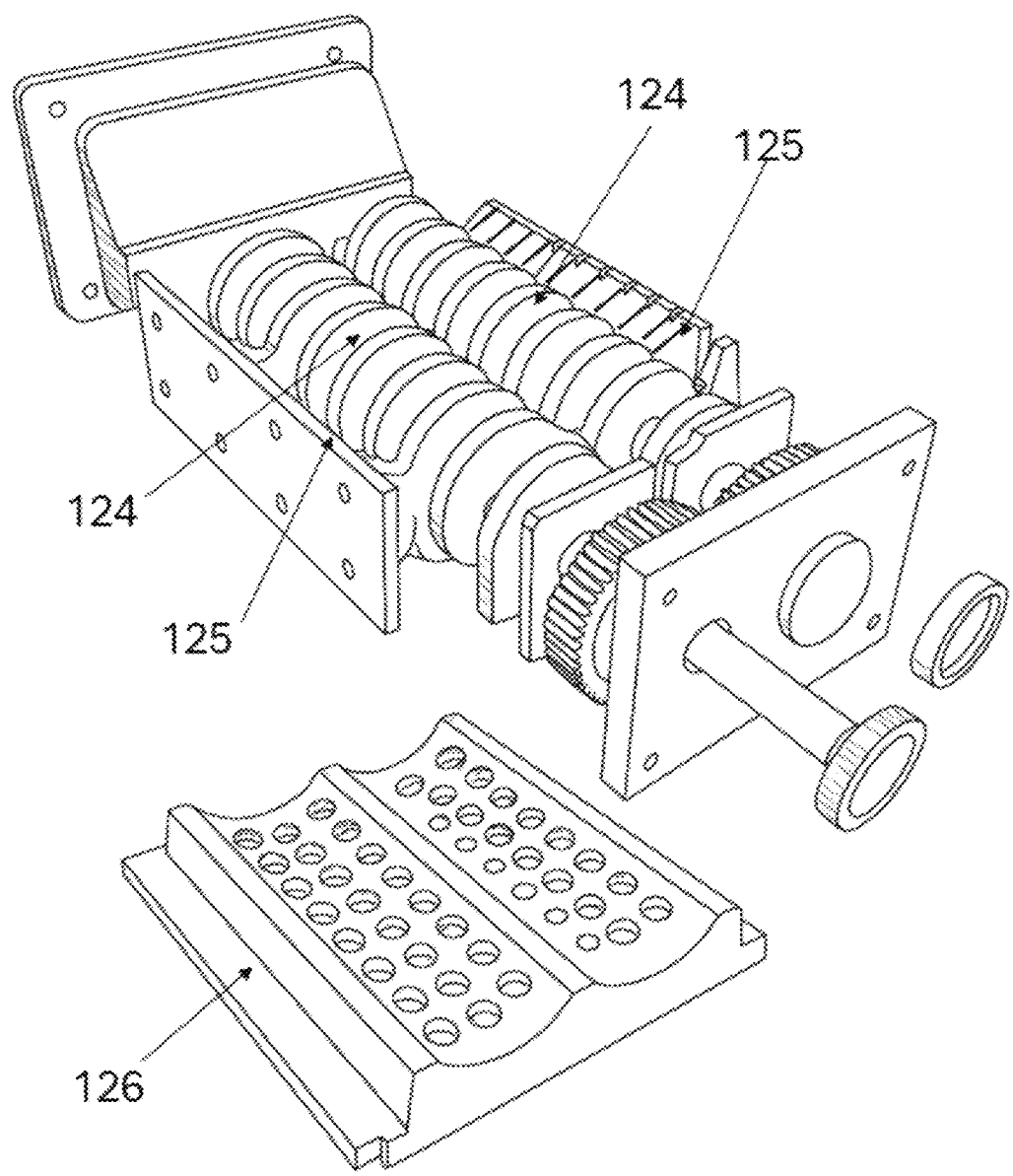
FIG. 4 shows a semi-exploded close-up of the shredder (123), showing the rotating shredding blades 124.

FIG. 4 shows a semi-exploded close-up of an embodiment of a shredding unit 123. In this embodiment, the shredding unit 123 comprises two shredding blades 124, where each shredding blade 124 comprises a plurality of cutting blades, the cutting blades mounted to a core, with the cutting blades perpendicular to the longitudinal (rotation) axis of the shredding blade 124. Preferably, the shredding blades 124 counter-rotate. Preferably, the shredding blades 124 rotate inwardly, drawing the waste into the gap between the pair of shredding blades 124. In some embodiments, at least one shredding blade 124 can rotate outwardly, for non-limiting example, to clear waste trapped between the shredding blades 124.

Preferably, each shredding blade 124 is associated with a shredding cleaning tooth assembly 125 comprising at least one cleaning tooth, which help to further shred the waste and help prevent sticking of waste to the sides of the shredding bin 121. Preferably, the shredding cleaning tooth assembly 125 is attached to the side of the cleaning bin 121 with at least one cleaning tooth being between two of the cutting blades of the associated shredding blade 124. In several embodiments, the shredding cleaning tooth assembly 125 further help the shredding procedure by enabling further tearing of specific types of waste (i.e. gauzes and medical waste containers) which usually get stuck in prior art machines, and by further crushing the waste. Under the two shredding blades 124, there is a first tray 126 having orifices. The orifices are of a shape and diameter (SD1) selected to ensure that only waste that is smaller than a desired size can pass through into the disinfection unit 130. In some embodiments, the diameter of the orifices is between about 16 millimeters and about 22 millimeters. The first tray 126 is configured to be easily replaceable, in case the orifices are obstructed by waste. One of the advantages of the present invention in comparison to prior art is that each shredding blade 124 can rotate independently of other shredding blades 124. For example, at least one shredding blade 124 can have a rotational velocity different from at least one other shredding blade 124, and at least one shredding blade 124 can have a direction of rotation different from at least one other shredding blade 124 (e.g., one clockwise, one anticlockwise, both clockwise, or both anticlockwise). This difference in rotational velocity and rotation direction enables not only the action of "crushing", but also the action of "tearing" of the waste. The "tearing" action is important for many types of medical waste (i.e. gauzes and medical waste containers).

Figure 5:
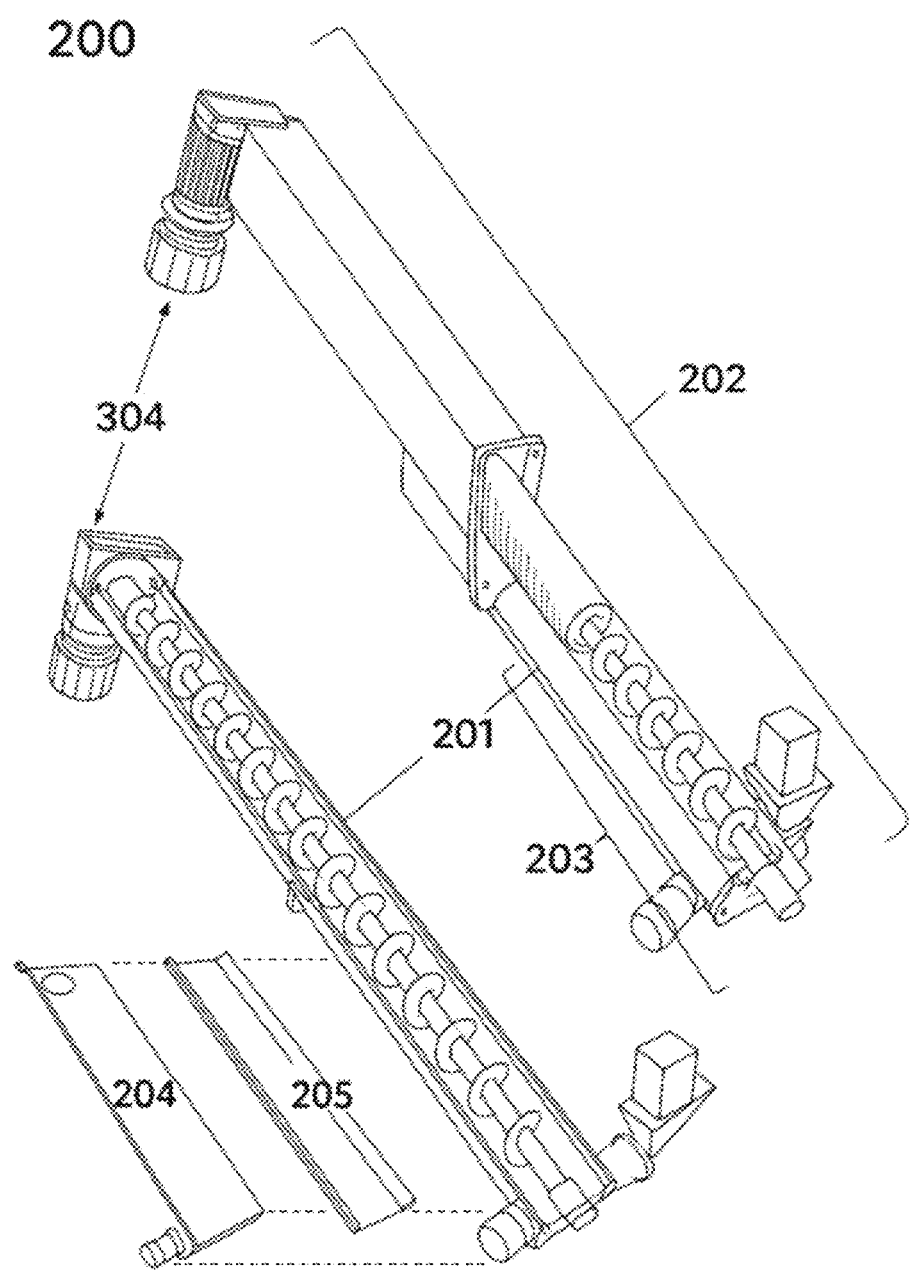
FIG. 5 shows an exploded view of the separator unit 200.

FIG. 5 shows an isolated view of an embodiment of the separator unit 200. The separator unit 200 is an integrated separator unit that separates the solid waste from the liquid. The unit comprises a long screw 201 located inside the separation arm 202. The lower part 203 of the separation arm 202 is open and is in continuous communication with the disinfectant mixing bin 131. Once the waste has finished the disinfection treatment, the screw begins to rotate by means of a motor 304. The movement of the long screw 201 inside the separation arm 202 "pushes" the waste up along the separation arm. The lower part 203 of the separation arm 202 comprises a panel 204 which holds a second tray 205 where used disinfectant liquid can drain (separated) from the treated solid waste. The tray works as a strainer. The used disinfectant liquid is drained via a dedicated liquid waste management unit 606. The second tray 205 also comprises a plurality of orifices of a shape and diameter (SD2) selected to ensure that only the used disinfectant liquid (without the waste) can pass through into the dedicated dusposal valve (606), while all the solid waste remains in the screw, inside the separation arm 202. Typically, the diameter of the orifices is between about 1 millimeter and about 10 millimeters. The second tray 205 is also easily replaceable, in case the orifices are obstructed by waste. Typically, most of the used disinfectant liquid is separated in the lower part 203 of the separation arm 202, but further separation of liquid from the solid waste occurs during the passage of the waste along the whole of the separation arm 202. The dedicated liquid waste management unit 606 comprises an exit valve (either analog or digital) which manages and monitors the evacuation rate of the used disinfectant liquid, thereby controlling the amount of waste entering the long screw 201 and avoiding overload of waste in the separation arm 202.

In some embodiments, the rotational velocity and the direction of rotation of the long screw 201 can be varied during the process. Such variation allows the long screw 201 to act as a centrifuge and further contributes to separation between the solids and the liquid.

Figure 6:
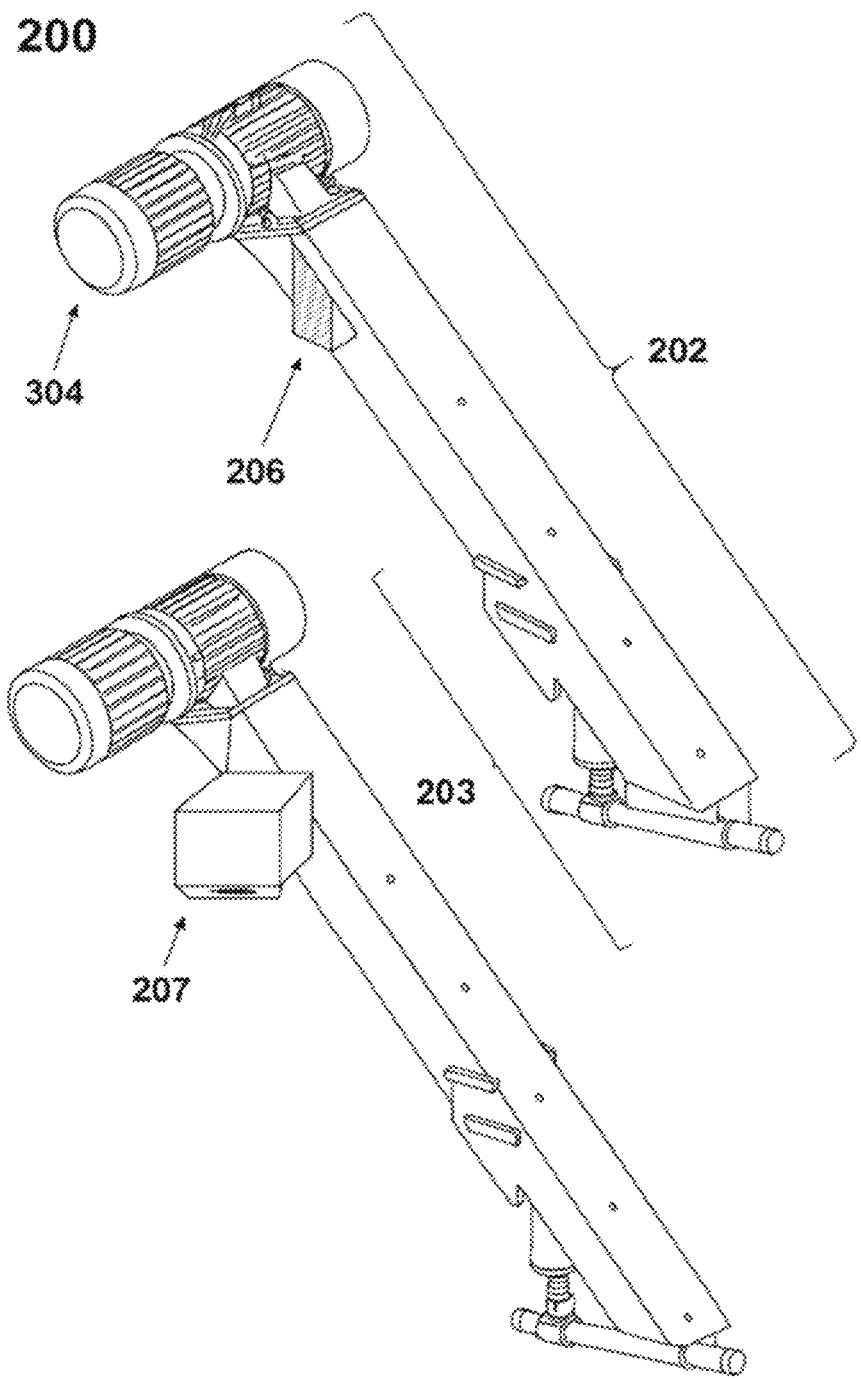
FIG. 6 shows another view of the separator unit 200.

FIG. 6 shows another view of the separator unit 200. In FIG. 6, the separation arm 202, the lower part 203 of the separation arm 202 and the motor 304 are shown. At the end of the long screw 201 there is an output chute 206 where the dry treated waste falls into a designated ordinary waste bin (not shown).

Integrated Centrifuge

In some embodiments, at the end of the separation arm 202 at the output chute 206, a mini-centrifuge 207 is installed. This centrifuge is configured to further separate the solid waste from the liquid. The centrifuge may further comprise a UV lamp to further contribute to disinfection. The liquid separated from the waste is directed to the dedicated liquid waste management unit 606.

Figure 7:
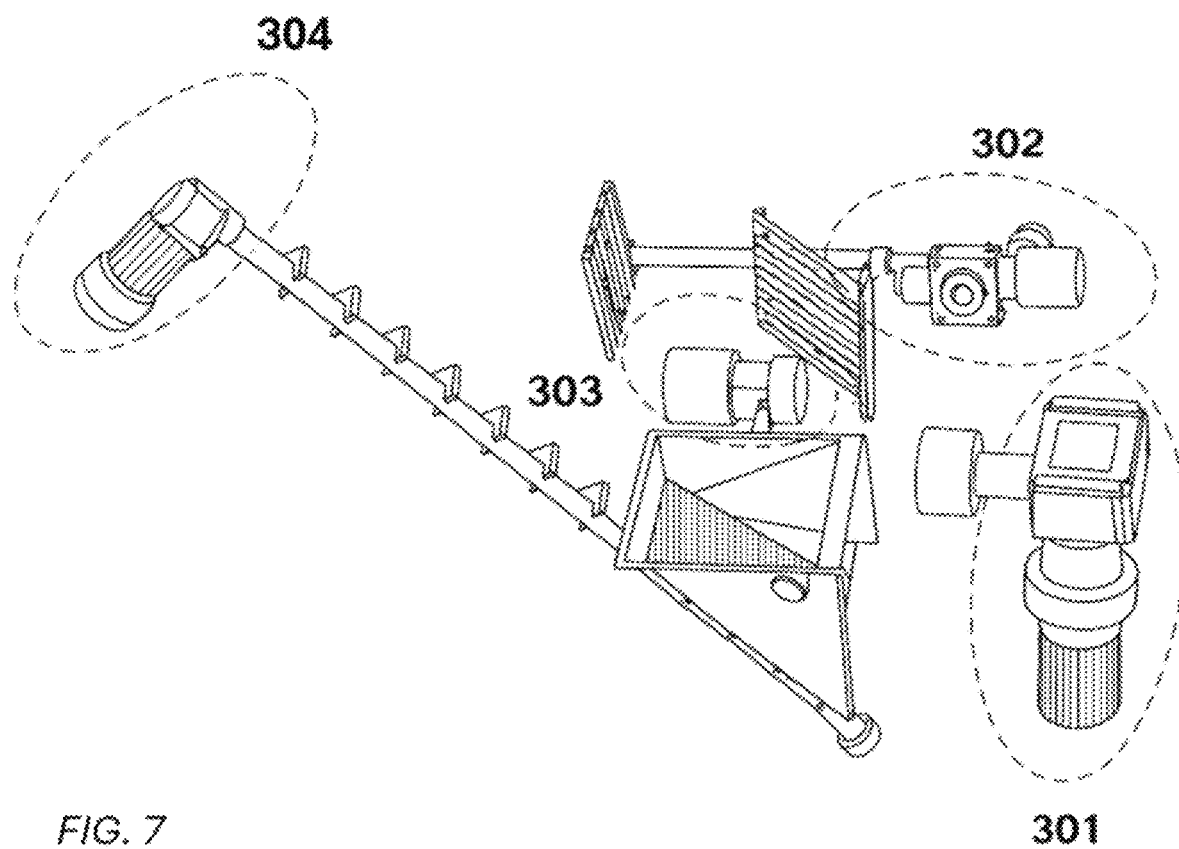
FIG. 7 shows a schematic view, not in scale, of the motor units 300.

FIG. 7 shows a schematic view, not to scale, of an embodiment of the motor units 300. The shredding motor unit 301 powers the rotating shredding blades 124. The compression motor unit 302 powers the compression unit 122. The mixing motor unit 303 powers the mixing unit 132 in the mixer bin 131. And, finally, the long screw motor unit 304 powers rotation of the long screw 201.

Figure 8:
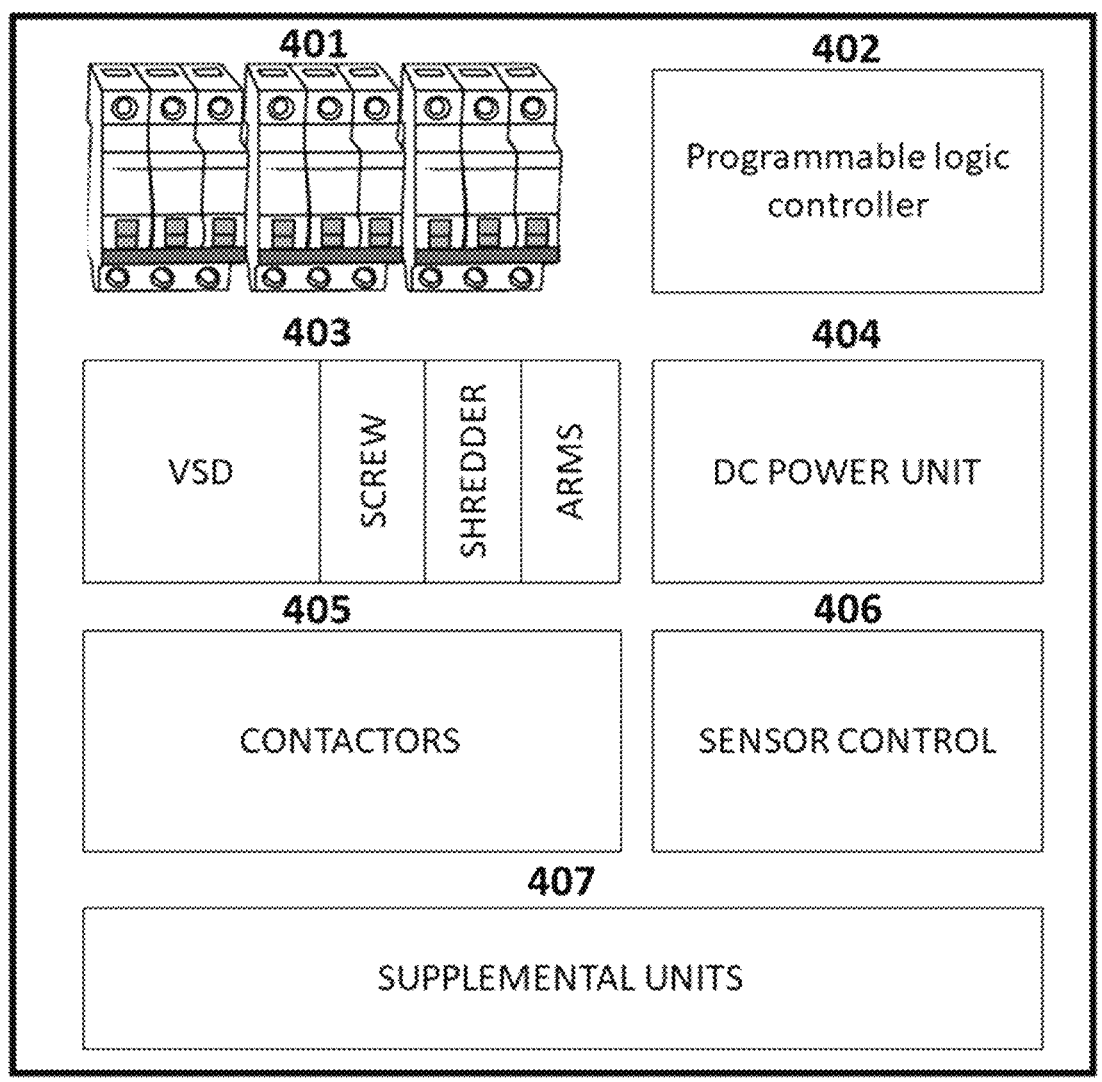
FIG. 8 shows a schematic view of the electrical unit 400.

FIG. 8 shows a schematic view of the electrical unit 400. The electrical unit comprises the electrical components needed for operation of the system. The electrical unit 400 comprises electrical breakers 401, a programmable logic controller 402, and at least one Variable Speed Drive (VSD) controller 403 for parts that require it, such as, but not limited to, the long screw 201, the shredding blades 124 and the compression unit 122. The electrical unit 400 also comprises a DC power unit 404 for the various controls (e.g., sensors, contactors and VSD), contactors 405 for the different parts, sensor control 406 for the at least one sensor (see below) of the system, and supplemental units 407, such as, but not limited to, a communication card (internet, wireless, etc.), dedicated hardware, and others.

Figure 9:
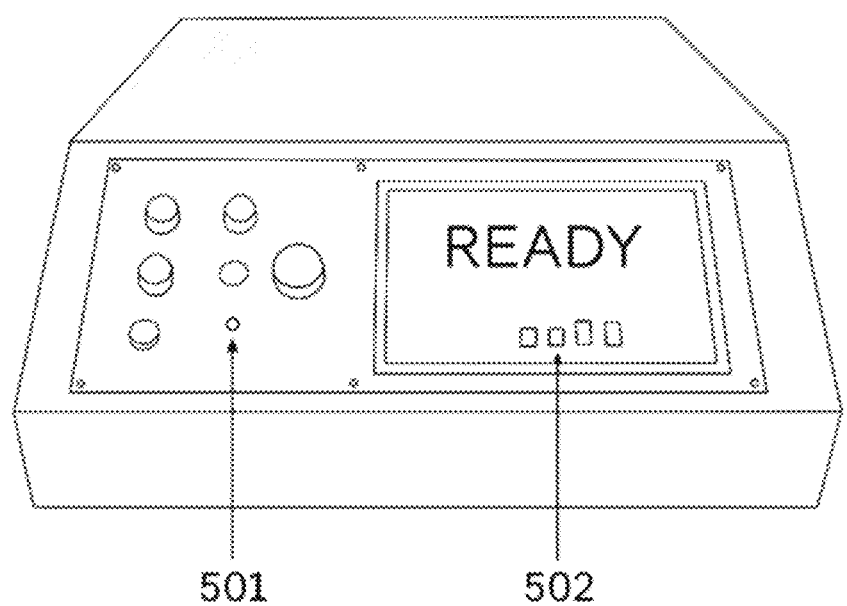
FIG. 9 shows a schematic representation of the operator panel unit 500.

FIG. 9 shows a schematic representation of an embodiment of the operator panel unit 500. The panel unit may comprise buttons 501, a touch screen 502, or a combination of both. The panel can also include an emergency stop button.

Figure 10:
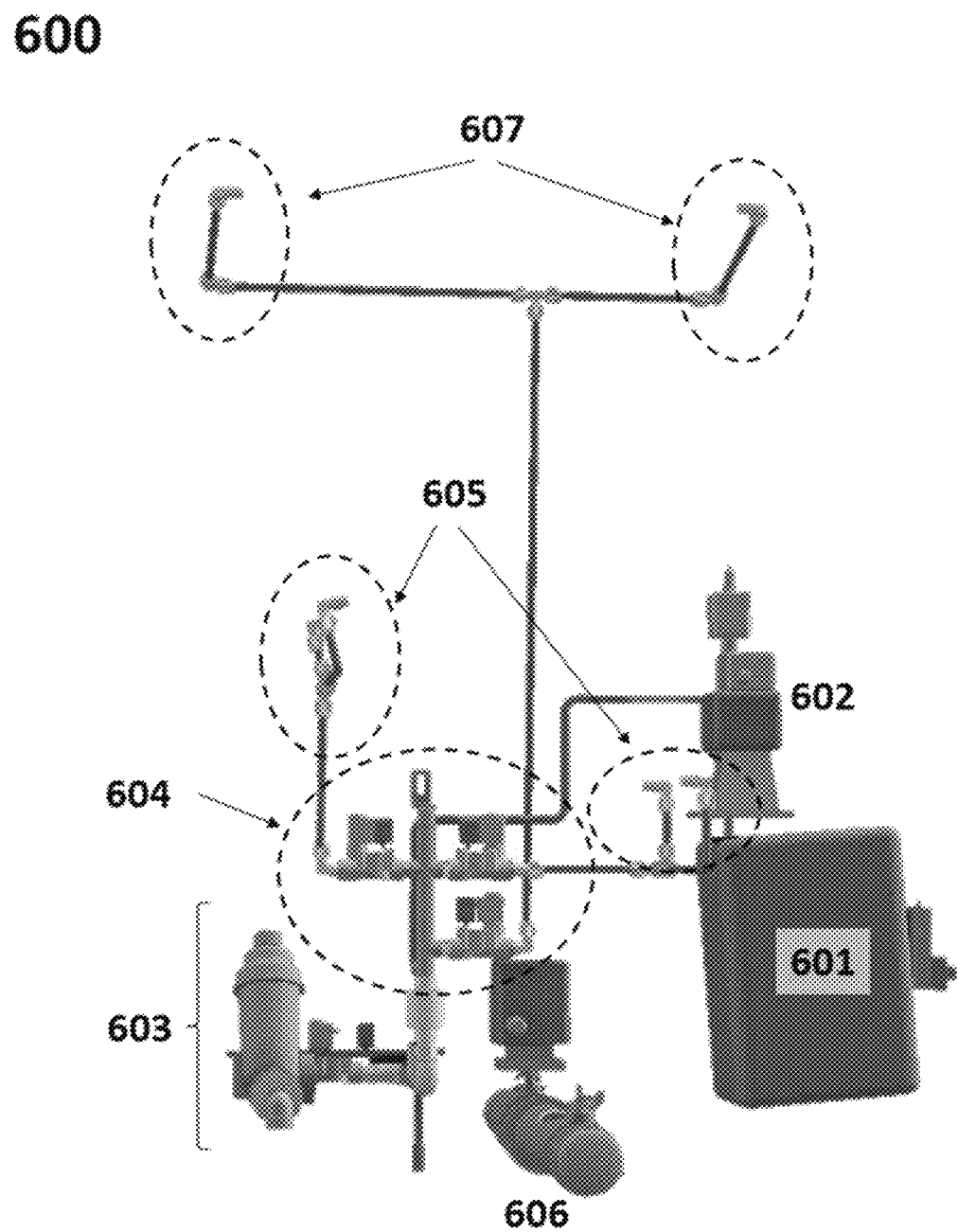
FIG. 10 shows a schematic, not to scale, view of the main liquid management unit 600.

The shredding system is coupled to a main liquid management unit. The main liquid management unit comprises a water/disinfectant mixing unit, a disinfectant delivery unit and a liquid waste management unit. FIG. 10 shows a schematic, not to scale, view of an embodiment of the main liquid management unit 600. The disinfectant concentrate is stored in a dedicated container 601. Attached to the container 601 is a pump 602, in some embodiments a micropump, configured to administer a predetermined ratio of disinfectant concentrate to water, where the quantity of water plus disinfectant concentrate is within predetermined limits. The water is typically tap water which can have been passed through a filter 603 for removal of large contaminants. The dedicated mixing unit 604 is configured allow mixing of the incoming water and the disinfectant concentrate. The mixing unit utilizes the natural vortex created by the movement of the water inside the tubes as a tool for mixing the disinfectant concentrate and the water. This way, the liquid that arrives at the dedicated delivery units as a ready to use as a disinfectant liquid, a "disinfectant concentrate/water solution". The dedicated delivery units are specialized nozzles 605 that disperse the disinfectant liquid inside the disinfection unit 130. Once the disinfection treatment is complete, the used solution is discarded via a dedicated liquid waste management unit 606, located in the bottom part of the separation arm 202. Another set of specialized nozzles 607 are located in the area of the waste receiver cover 110 and the waste shredding unit 120 in order to perform post-treatment disinfection of areas that a user may come in contact with. This post-treatment disinfection is performed after each cycle, where a cycle starts with closure of the waste receiver cover 110 and ends when substantially all of the waste has passed to the designated ordinary waste bin. The use of nozzles is an inventive feature over the prior art systems. The nozzle system enables the exposure of the waste to the disinfectant liquid while the waste is still in the first tray, ensuring that all the waste and every part of the waste comes in contact with fresh, unused disinfectant liquid. The number of nozzles can vary, depending on the size of the machine.

Figure 11:
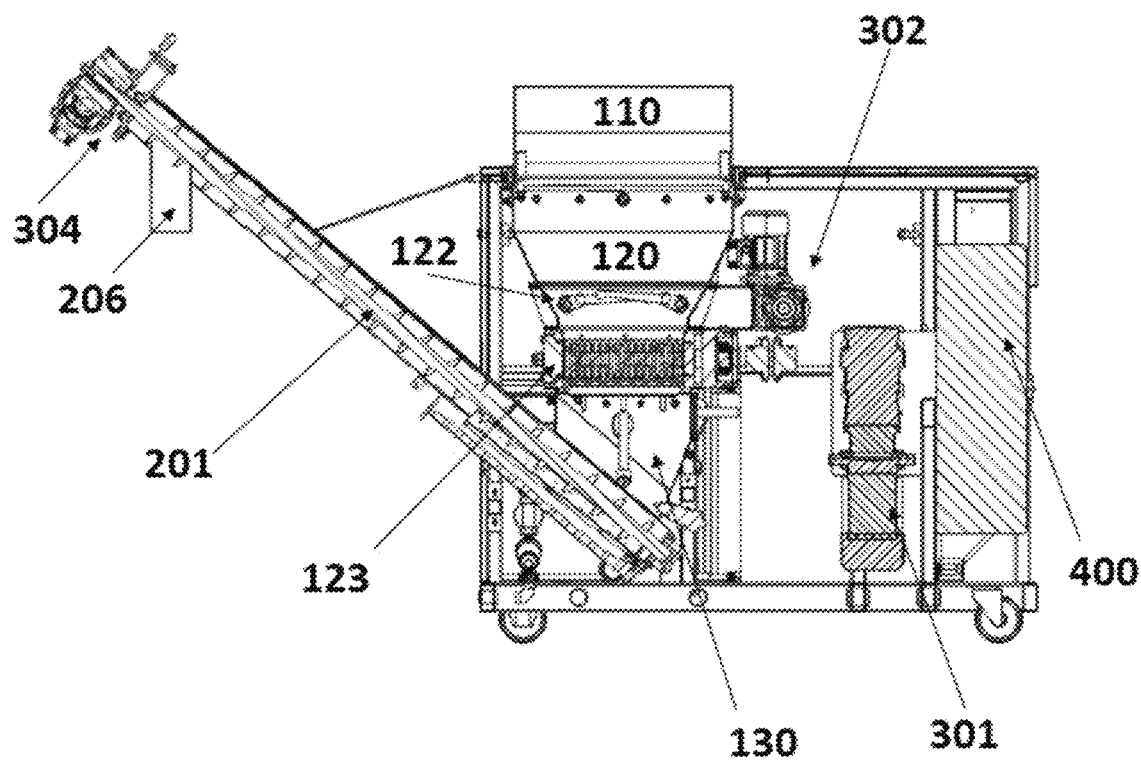
FIG. 11 shows another schematic representation of the system 1000.

FIG. 11 shows another schematic representation of the system 1000, illustrating key parts of the system.

FIGS. 12-17 show another embodiment 1100 of the B. M. W. disinfecting shredder system. This embodiment comprises modifications from the embodiment disclosed above, the modifications configured to increase the efficiency and flexibility of the disinfecting shredder system.

The modified embodiment 1100 can comprise a printer for logging on-line parameters. Output can include the amount of water used, the amount of disinfectant used, other disinfectant data such as, but not limited to, disinfectant batch number and expiry date, temperature of the liquid/waste mixture at predetermined times during processing, average temperature, shredding time, mixing time, and weight of the waste. Processing data can also be stored in a database, as disclosed above.

At least one test port has been provided for on-line real-time qualification and validation, so that tests can be performed at at least one point during the process without the need for an external laboratory. Tests can comprise physical examination, particle size of the shredded waste, pH of the liquid, compliance with predetermined chemical parameters, and microbial performance The modified embodiment 1100 preferable comprises a plurality of load cells (not shown) to weigh the waste and waste/liquid mixture at different stages of the process. A load cell can be associated with a member of a group consisting of the loading container 140, the shredding unit 120, the sump 660, the liquid/waste separation system 1200 and any combination thereof.

Flow, pressure and temperature sensors have been added.

Figure 12:
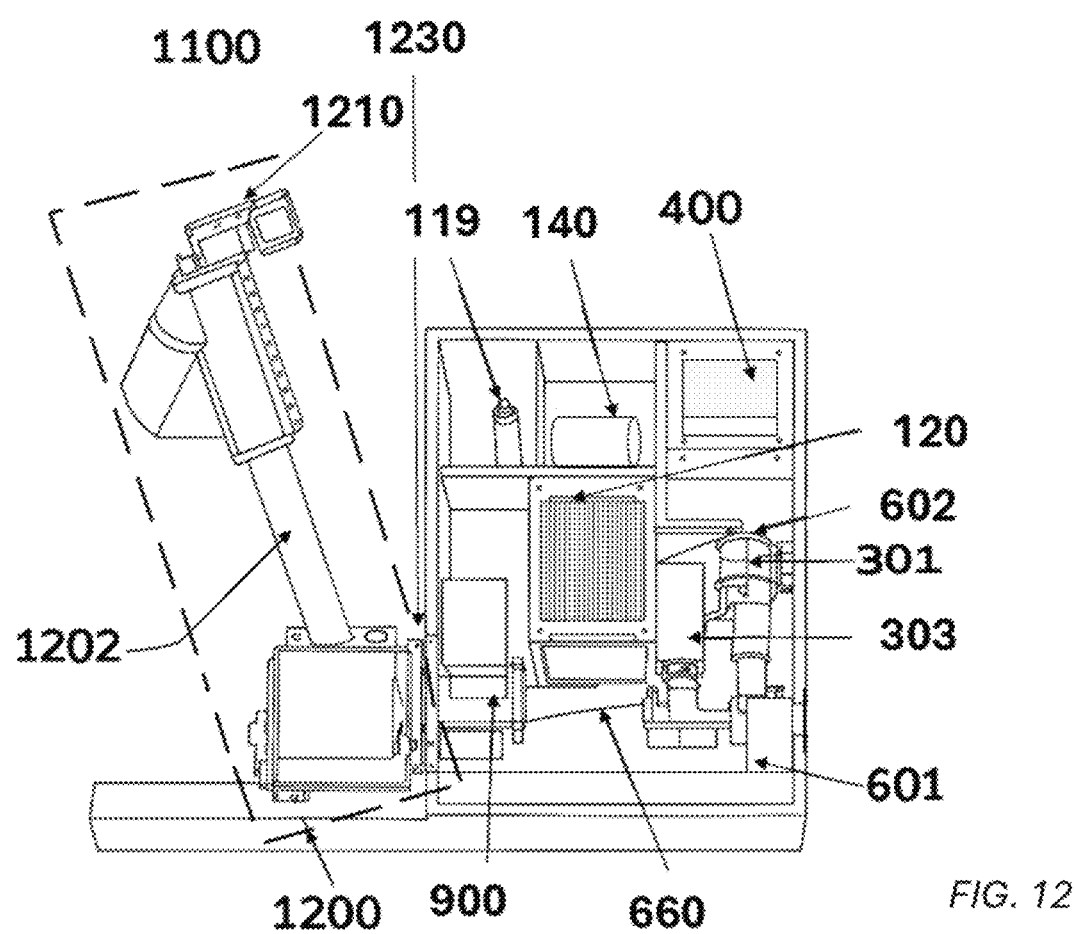
FIG. 12 shows a view of a modified embodiment 1100 of the system.

FIG. 12 illustrates the main features of this embodiment 1100. Waste is loaded into a loading container 140. After loading is complete and the lid is closed, the waste can pass to the shredding unit 120. Lid closure can be either manual or automatic; in the embodiment shown, a lid closure motor 119 ensure proper closure. The lid can be closed to a sealing level of IP65 or IP67. After the waste has entered the shredding unit 120, volumetric dosing pump 602 removes a measured amount of disinfectant concentrate from container 601, mixes it with a measured amount of water in volumetric dosing pump 602 (and passes the disinfectant liquid into the shredding unit 120. Mechanical volumetric dosing pumps of this type are not sensitive to air in the system, thus increasing reliability without losing accuracy. The shredding unit motor 301 is simultaneously starts to shred the waste. When sufficiently shredded, the waste is pressed by the shredding blades 124 through a grating 126 to the sump 660, for further mixing of disinfectant and waste. The mixing is driven by a mixer motor unit 303. The exit to the sump is closed by a valve 900 (analog or on-off valve), which opens when the mixing is complete. The valve 900, controlled by the software, is connected to the sump 660 by a flexible hose, to ensure accurate and stable weighing of the material in the sump 660 and complete vibrational separation of the sump and the liquid/waste separation system 1200. In preferred embodiments, the valve 900 is a 4 inch valve matched to a 4 inch flexible hose. The valve diameter and the hose diameter can be in a range from 2 inches to 10 inches, depending on the size of the system.

As disclosed above, at least one nozzle (not shown, 607) dispenses disinfectant liquid into the loading container 140 and/or the shredding unit 120 to ensure that areas contactable by a user are decontaminated before a user can contact them. A valve separates the long screw conveyor 1202 from the sump 660 so that, as soon as the waste has been cleared from the sump 660, the valve can be closed so that new waste can be loaded in the loading container 140 and a new processing cycle can be started while the screw conveyor is still working, thus shortening the cycle time.

The electrical unit 400 also comprises a DC power unit 404 for the various controls (e.g., sensors, contactors and VSD), contactors 405 for the different parts, sensor control 406 for the at least one sensor (see below) of the system, and supplemental units 407, such as, but not limited to, a communication card (internet, wireless, etc.), dedicated hardware, and others.

After the valve 900 and before the liquid/waste separation system 1200 is a suction unit (not shown) to ensure complete removal of the liquid/waste mixture from the sump 660.

In preferred variants, if the temperature of the liquid/waste mixture in the sump 660 is outside a predetermined range, the system stops and a fault notification is generated. In some variants, the system stops until a temperature regulation mechanism (not shown) brings the temperature within the predetermined limits. The predetermined range is from 10 degrees C. to 40 degrees C.

Figure 13A:
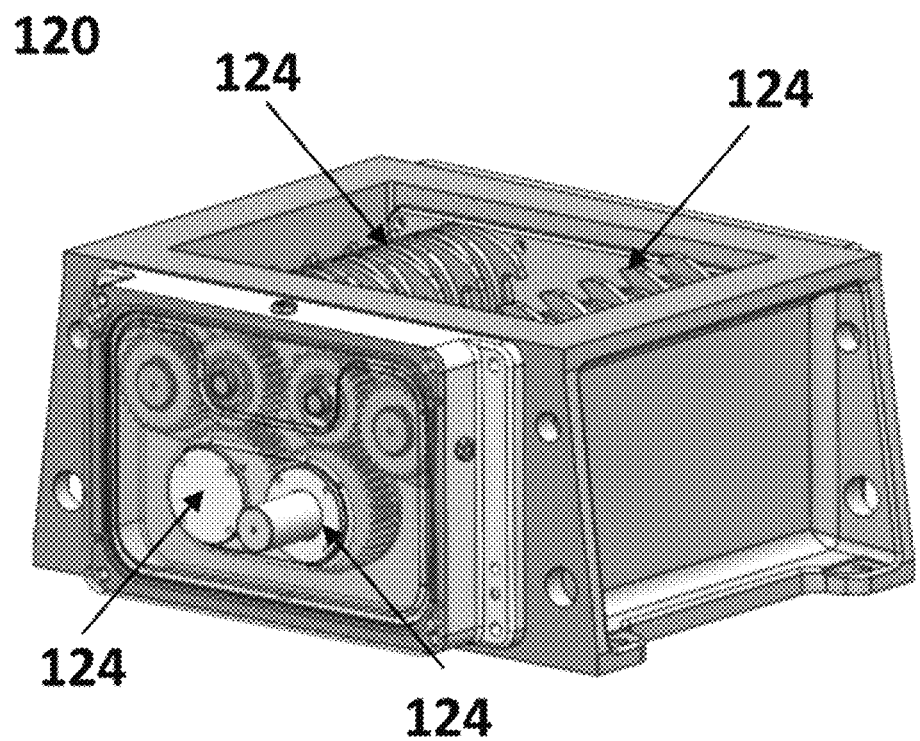
FIGS. 13A-B show the shredder unit 123.
Figure 13B:
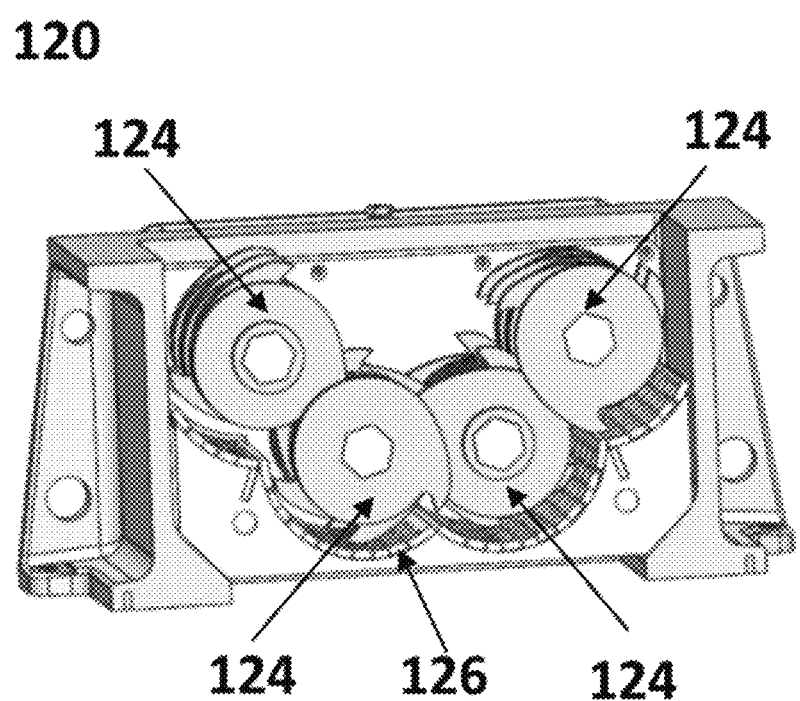

FIG. 13A-B shows an embodiment of the shredding unit 120. FIG. 13A shows the exterior of the shredding unit 120 while FIG. 13B shows a cutaway view. In this variant, the shredding unit 120 comprises four shredding blades 124. The number of shreddingr blades 124 can be in a range from 2 to 10; more shredding blades 124 allow more aggressive shredding. The number of cutting blades on a shredding blade 124 can be in a range from 32 to 100; more cutting blades allow more aggressive shredding. In some embodiments, at least one shredding cleaning tooth assembly 125 is provided, as disclosed above. In the embodiment shown, a pressing plate (not shown) is used instead of closing arms to compress the waste.

Figure 14:
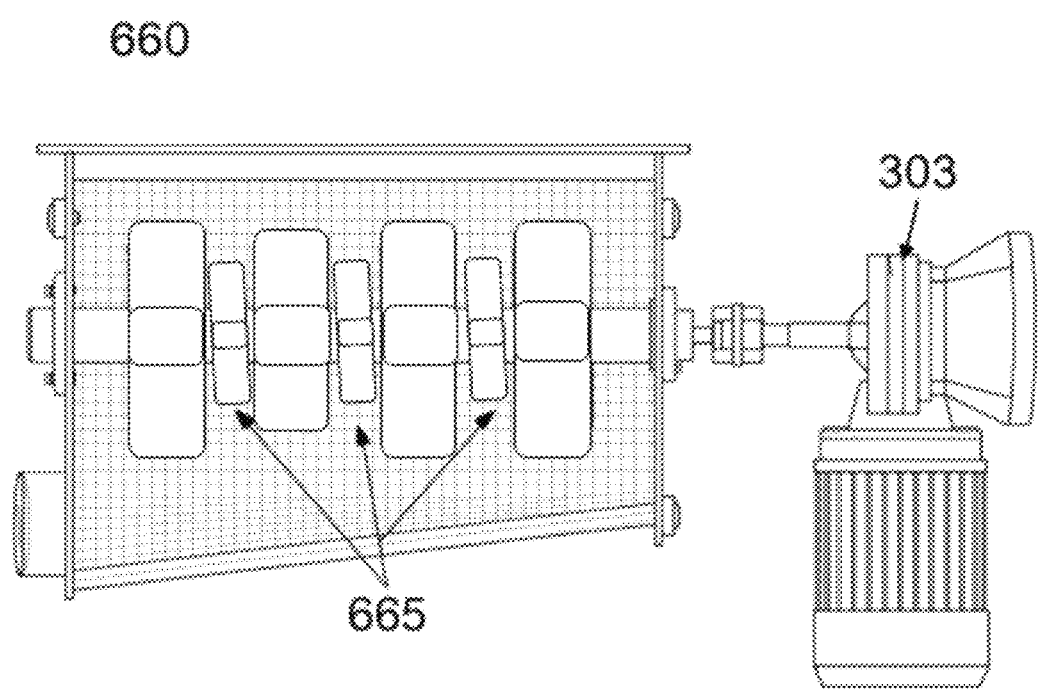
FIG. 14 shows a view of the sump 660.

FIG. 14 shows an embodiment of the sump 660. The sump comprises a plurality of impellers 665 driven by a mixer motor unit 303. A larger number of impellers ensures more even and more aggressive mixing. The number of impellers can also depend on the size of the system; the larger the system, the more impellers. The number of impellers can range from 2 to 40.

In some embodiments, the sump 660 comprises at least one nozzle (not shown), ensuring maximum disinfection with fresh disinfectant. Preferably, a plurality of nozzles is used for more even mixing.

In preferred embodiments, the water system comprises at least one ultrasonic sensor to control dispensing of the disinfectant liquid. This increases the flexibility and reliability of the system.

The ultrasonic sensor system is convenient to operate, reduces the number of connectors, thus reducing the probability of leaks in the system.

In preferred embodiments, the sump 660 comprises an openable window (not shown) to allow easy and rapid replacement of the impellers. The window can be transparent, translucent or opaque; in some embodiments, a transparent window allows observation of the functioning of the impellers.

Figure 15A:
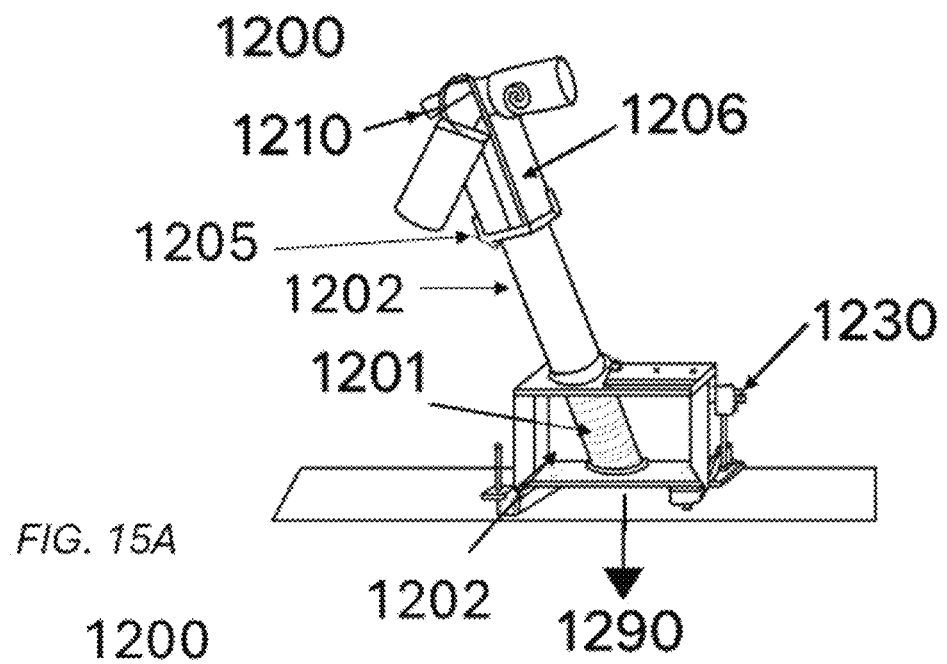
FIGS. 15A-b shows the separator unit 1200.
Figure 15B:
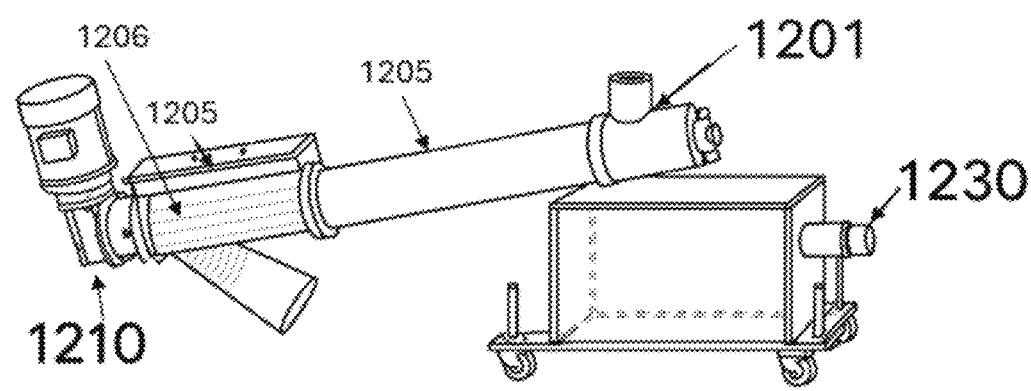

FIG. 15A-B shows an embodiment of the liquid/waste separation system 1200. In FIG. 15A, the liquid/waste separation system 1200 is shown in its operating position, while in FIG. 15B, the liquid/waste separation system 1200 is shown dismounted for any of cleaning, maintenance or repair. The liquid/waste mixture enters liquid/waste separation system 1200 via the quick release valve 1230 and passes into a holding tank 1209. It then enters the lower part of the separator, which comprises a sieve 1201, a long screw conveyor 1202 and a mechanical squeezer 1205. From the sieve, is passes into the long screw 1202, which has 1 to 5 mm holes, for separation of the waste from the majority of the liquid. In the upper portion of the separator is a mechanical squeezer 1205 to further minimize the amount of liquid in the waste. In this embodiment, the mechanical squeezer 1205 comprises a screw 1206. A gear motor 1210 powers the long screw conveyor 1202 and the mechanical squeezer 1205. The system can also comprise a centrifuge after the mechanical squeezer 1205. Waste liquid passes 1290 to the liquid waste disposal, as disclosed above, via the bottom of the holding tank 1209.

In preferred embodiments, no tools are needed to tilt the liquid/waste separation system 1200 from its operating position to its dismounted position, increasing the ease of maintenance.

In preferred embodiments, the liquid/waste separation system 1200 can operate when disconnected from the rest of the system by means of the quick connector 1230.

Since the liquid/waste separation system 1200 is not part of the disinfection system, a new disinfection cycle can be initiated before completion of separation of the spent disinfection liquid and the waste, thus shortening cycle time for the process and thereby increasing throughput.

Temperature can be measured for a member of a group consisting of incoming water, the disinfectant concentrate, the liquid exiting the nozzles, material in the loading chamber, material in the shredding chamber, material in the sump, material in the liquid/waste separation system and any combination thereof.

Flow rates can be measured for the disinfectant concentrate, for the water, for the material exiting the shredding unit, material exiting the sump, liquid exiting the liquid/waste separation system, waste exiting the liquid/waste separation system and any combination thereof.

In preferred embodiments, at least one temperature control system can maintain the temperature in a predetermined range for a member of a group consisting of the disinfectant concentrate, the incoming water, the liquid exiting the nozzles, the material in the shredding chamber, the material in the sump, the material in the liquid/waste separation system and any combination thereof.

In preferred embodiments, connections are by means of quick connectors, as illustrated by the quick connector between the sump and the suction system and the connection between the suction system and the liquid/waste separation system 1200.

Figure 16:
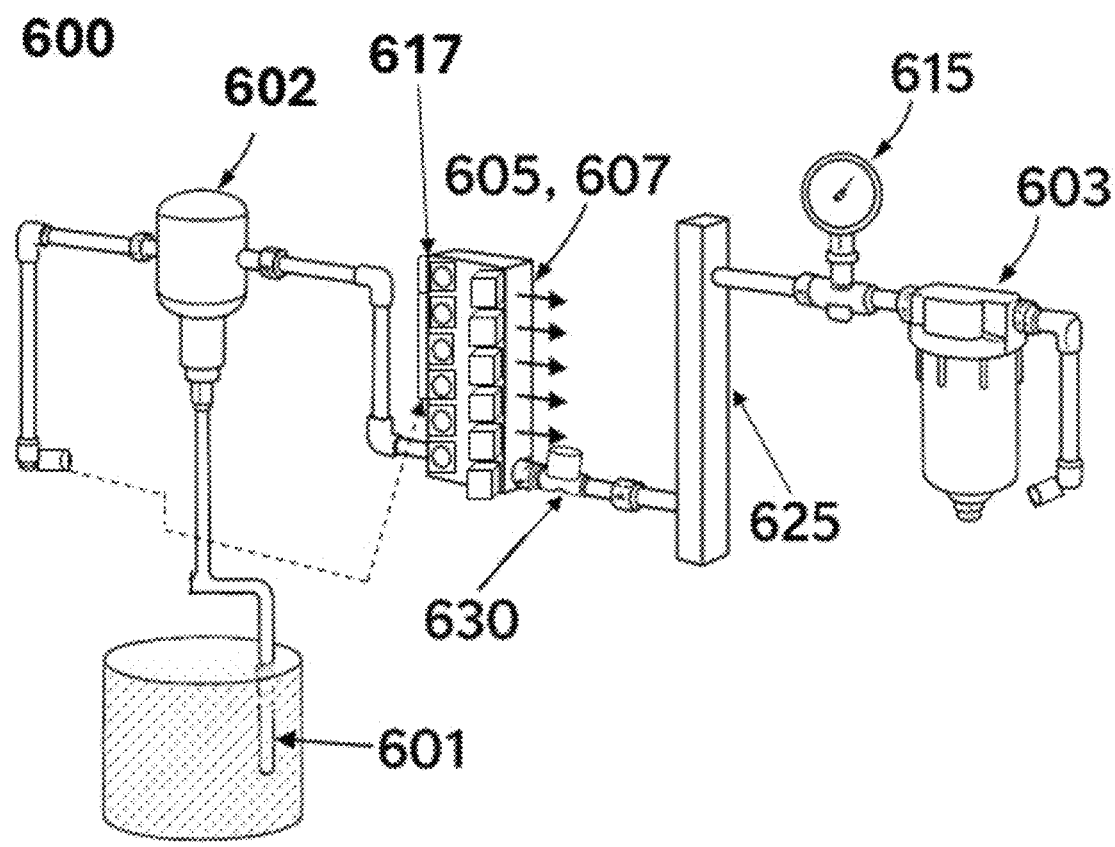
FIG. 16 shows schematic, not to scale, view of the main liquid management unit 600.

FIG. 16 illustrates, in an out-of-scale manner, an embodiment of a main liquid management unit 600 of the modified embodiment 1100. Incoming water passes through a filter 603, through a valve (on-off or analog valve) and pressure sensor 615 through a temperature control unit 625, preferably an on-demand water heater, and then through a flow rate regulator 630. The disinfectant concentrate is pumped from the concentrate container 601 via pump 602 to the ultrasonic sensor 617 where it is mixed with the incoming water and exits, via at least one of the nozzles 605 and 607, into at least one of a group consisting of the loading container 140, the shredding unit 120, the sump 660, and any combination thereof.

Sensor Units

Several parts of the system comprise dedicated sensors which allow the system to work in perfect synchronicity and at the highest efficiency possible.

A unit can have one or more functions to be evaluated, and each function can be evaluated by one or more sensors. For simplicity and clarity, the one or more sensors, which can be of different types, will be referred to as "the sensor" or "a sensor". Again, for simplicity and clarity, the terms "the sensor" and "a sensor" will comprise the physical sensor which generates a signal and any software needed to process the signal, Waste receiver cover sensor: the sensor in the cover shows if the cover has been properly closed before allowing the system to begin the treatment cycle. It is a special safety element.

Compressing Unit Sensor

In embodiments with closing arms: A sensor, typically a resistance sensor, to detect whether the closing arms can perform properly. In case too much waste has been inserted and the closing arms cannot perform properly an alarm message is generated. This sensor typically is also configured to evaluate the quantity of waste that is still in the waste shredding unit. This information is used to command the activity of the shredders, although a separate waste-quantity sensor, such as (but not limited to) a level sensor, can be used.

In embodiments with a pressing plate: A sensor, typically a resistance sensor, evaluate the force needed to push the waste towards the shredder. In case too much waste has been inserted and the pressing plate cannot perform properly an alarm message is generated. A sensor, typically a level sensor, to indicate at least one of: when all the waste has been shredded and what quantity of waste is still in the waste shredding unit. This information is used to command the activity of the rotating shredding blades.

Rotating shredding blades sensors: Typically a "shredding motor current sensor". An abnormal increase in current may mean that waste is resisting shredding. In this case, at least one shredding blade 124 will be rotated in an opposite sense (e.g., anticlockwise instead of clockwise) for a predetermined time in order to loosen the waste from the shredding blades 124. If this event happens too many times in a predetermined time period, shredding will be stopped and a fault announcement generated. This control algorithm provides smooth, effective and long-lasting shredder performance First and Second tray sensors: these sensors check the correct positioning of the first and second trays. If to tray is not in place or is not placed correctly, the system is stopped.

Disinfection Unit Sensor

In some embodiments, the mixing bin has an "optimal capacity", one in which the ratio between the waste and the disinfectant is optimal, and the mixing bin contains the optimal quantity of material that can be mixed therein. The system assesses these optimal ratios and optimal quantities by a variety of sensors.

In other embodiments, the volume of the mixing bin is known. The system comprises a flowmeter that measures exactly how much water is delivered to the disinfection unit. The system further comprises another flowmeter which measures exactly how much disinfectant is delivered. Using these three parameters and an analog height sensor, the system calculates the volume of waste which entered the mixing bin. This is a unique embodiment since this allows to monitor exactly the volume of waste that has been shredded.

In some embodiments, the disinfection unit sensor comprises a volumetric sensor that measures the volume (or quantity) of material entering the mixing bin. This sensor can measure the weight of the material in the bin, can assess how full the bin is, and any combination thereof. The unit can also comprise an optical (or infrared) sensor capable of measuring the quantity of waste that exits the first tray. The system knows the optimal waste/disinfectant ratio and provides the right quantity of disinfectant through the nozzles.

In all embodiments the optimal ratio between waste and disinfectant liquid is between about 1:1 and about 1:3. This way, the system is configured to monitor in real-time the quantity of waste that is been shredded, the quantity of disinfectant liquid required for that amount of shredded waste, and the moment the mixing bin arrives at its optimal capacity for the treatment. Once an optimal capacity for the treatment has been attained in the mixing bin, the rotating shredding blades are disengaged so that they stop rotating.

Long screw sensor: the sensor provides real-time information on the performance of the long screw and provides a warning if the performance of the long screw is outside of predetermined limits, for example, if the long screw is not rotating properly.

Disinfectant RFID sensor: this sensor provides information on the disinfectant being used by monitoring the disinfectant container. The sensor checks if the container uses original chemical (disinfectant) produced by a validated producer and the expiry date of the chemical. If any of the following is true: non-original disinfectant concentrate is present, the container is from a non-validated producer, or the disinfectant concentrate has passed it expiry date, then the system will be stopped and a fault announcement will be provided.

Disinfectant

The recommended decontaminating disinfectant is a proprietary product called BIOCETIC, developed for HYGIMED. The concentration of BIOCETIC during the disinfection and treatment cycle is preferably from about 0.5% to about 2% of the total volume of liquid, depending on the type of waste. The BIOCETIC solution is contained in container 601 and fed into the different locations through the main liquid management unit 600. The decontaminating disinfectant is a room temperature disinfectant based on synergistic effect in a per-oxy compound mixture, having the following advantages over prior art disinfectants:

2. Broad microbiological efficacy
3. Low application concentration
4. Efficient at low application temperatures
5. Easy to rinse
6. Ecologically friendly
7. Protects machine black iron parts (e.g. shredding blades) from the acidity of the active substance, thus enabling a long expiration time for these parts.

The main activators of the composition of the decontaminating disinfectant BIOCETIC concentrate are as follows:

| Constituent | Concentration range |
| --- | --- |
| Acetic acid | 10-30% |
| Peracetic acid | 5-15% |
| Hydrogen peroxide | 5-15% |
| Caprylic acid | 1-5% |

Software and Cloud Services

The whole system is controlled by dedicated software that ensures correct and optimal performance of the system. The software controls all of the components and sensors. Preferably, the system is in communication with a central cloud-based station and sends and/or receives compliance data, updates, commands and other information. In -preferred embodiments, the central station is comprised within the system, with communication over a network to external sources, which can be cloud-based, for compliance data, updates, commands and other information, A user can access information, including cloud based information, via the operator panel unit 500. Communicated information can include information regarding the number of cycles attempted by the system, the number of cycles completed by the system, automated ordering (for example, of consumables), automated payment, details of the performance of the equipment, and a maintenance status for each piece of equipment. Preferably, technicians can be proactively dispatched to improve equipment availability, and reliable time stamping of equipment failure events can be provided for tracking repair technicians' performance. The Cloud services provide traceability. Including traceability of technical performance operational efficiencies and chemical allowance and exact usage according to specification, at least some of these parameters being available to users, with restricted access as appropriate, for example, for a technician, the owner, a distributor and also for regulatory inquiries.

"E-Regulatory" Compliance

For installations where waste treatment logs are maintained, all treatment data can be dispatched wirelessly to each client via the wireless communication system. Daily, weekly, monthly or annual treatment logs can be stored online at a server, and can be e-mailed to each client as a PDF or other appropriate file type, thereby replacing the need for printed paper treatment logs generated by a side-car stand-alone printer. PC connectivity, as opposed to Internet connectivity, is also available, allowing the unit to send parametric and treatment logs directly to a connected PC in the facility for regulatory reporting.

Routine Preventive Maintenance Reminder Services

Typically, routine preventive maintenance must be carried out. The bi-directional wireless communication capability and interface to the equipment allows service reminders to be sent to and from the equipment so that maintenance service can be acted upon in a timely manner at the deployed site. Once equipment maintenance has been performed, the service reminder warning on a system can be turned off (either manually or automatically), and record of the maintenance performed can be automatically generated. Preferably, an electronic database of maintenance logs comprising the records of maintenance for each system is provided, typically at a central cloud-based station. The database can be used to verify compliance with a service contract, and to record maintenance for regulatory compliance in markets where service records must be recorded.

Methods

Figure 17:
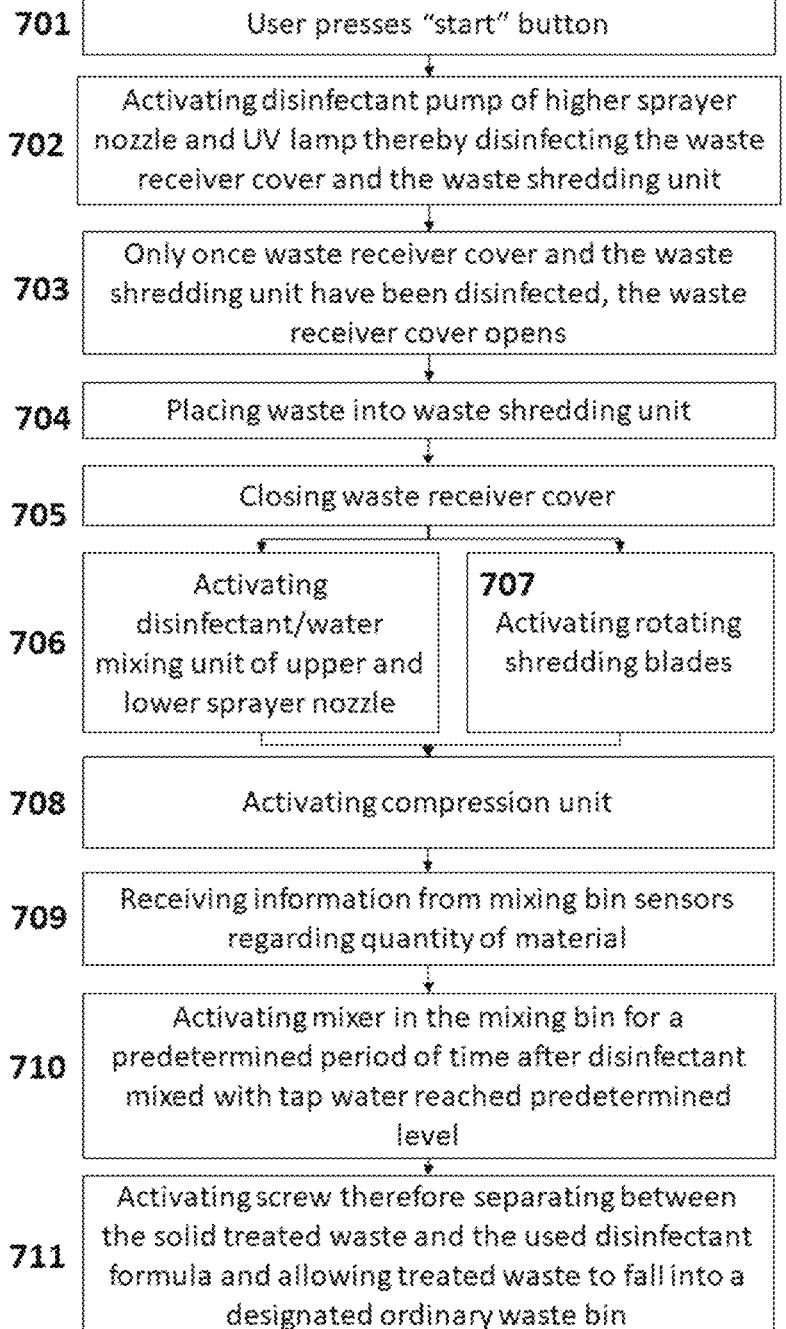
FIG. 17 shows a generic flowchart of the method 700 of the present invention.

FIG. 17 shows an embodiment of a generic flowchart of the method 700 of the present invention, which comprises the following steps:

1. Pressing the "start" button (by user) 701 in the operator panel unit.
2. Activating 702 the disinfectant/water mixing unit causing the disinfectant formula to exit through the higher sprayer nozzles, and activating a UV lamp in the waste receiver cover, thereby disinfecting the waste receiver cover and the waste shredding unit
3. Once disinfection is finished, opening 703 the waste receiver cover and placing 704 the waste in the waste shredding unit.
4. Closing the waste receiver cover 705.
5. Activating 706 the disinfectant/water mixing unit causing the diluted disinfectant formula to exit through the upper and lower sprayer nozzles, and concurrently activating 707 the rotating shredding blades. Spraying through the upper sprayer nozzle stops when shredding stops.
6. Activating 708 the compression unit.

7. Receiving information 709 regarding the quantity of material in the mixing bin from the sensors.
8. After disinfectant mixed with tap water has reached a predetermined level, activating 710 the mixer propeller in the mixing bin for a predetermined period of time
9. After a predetermined mixing time has elapsed 711, activating the long screw, thereby transporting the treated waste upwards along the separation arm.
10. Separating 711 the solid treated waste from the used disinfectant formula.
11. Further 711 transporting the treated waste upwards along the separation arm until the solid treated waste reaches the output chute where the solid treated waste can fall into a designated ordinary waste bin or can pass through a centrifuge for further separation of the fluid from the solid waste.

Some embodiments comprise a centrifuge at the end of the separation arm, for further separation of the fluid from the solid waste. In such embodiments, once the long screw has been activated, the centrifuge can also be activated. The centrifuge can operate in a pulsed mode or a continuous mode. In continuous mode, the centrifuge can start operation at the same time as the long screw or it can start at a predetermined time after the start of operation of the long screw. The centrifuge can stop operation before the long screw, at the same time as the long screw, or after the long screw stops operating. In pulsed mode, the centrifuge can start a first pulse at the same time as the start of operation of the long screw, or after the start of operation of the long screw. The last pulse can end before the long screw stops operating, at the same time as the long screw stops operating, or after the long screw stops operating., The method above describes generally the steps that the system performs during each cycle. Below, a detailed explanation of the actions and logic of the software will be described. FIGS. 13-15 show an embodiment of a flowchart 800 of the actions and logic of the software for the main activities.

Figure 18:
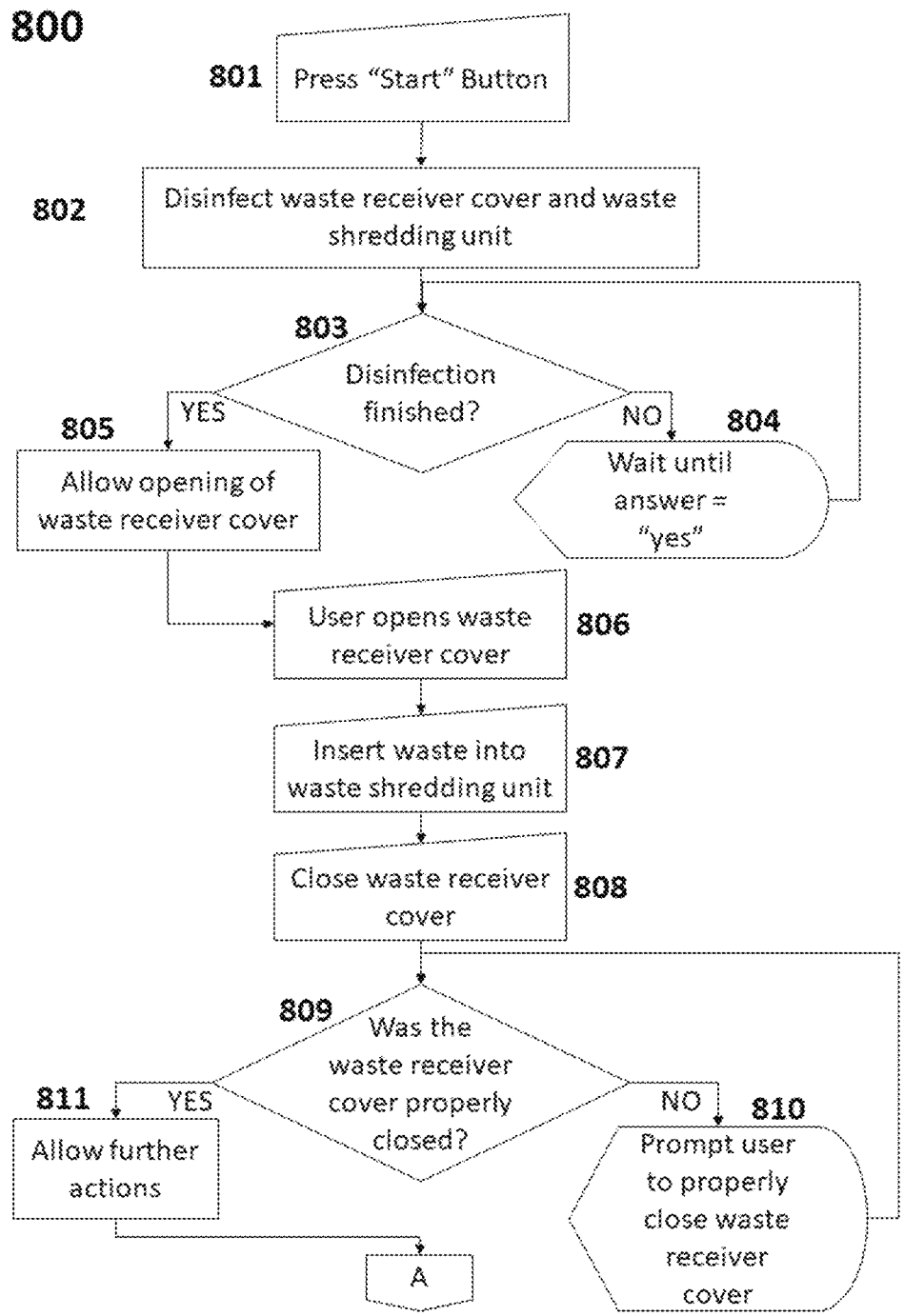
FIGS. 18-20 show a flowchart 800 of the actions and logic of the software for the main activities.

The chart of FIG. 18 starts from the time the system recognizes that the "start" button has been pressed 801. At this point, the system commences the safety disinfection procedure of the waste receiver cover and the waste shredding unit 802. The system then checks if the waste receiver cover and the waste shredding unit have been disinfected 803. If the answer is "no", then the system waits until the answer is "yes" 804. At the end of the disinfection process, the system will check again 803. If the answer is "yes", the waste receiver cover will be allowed to be opened 805. The user can then open the cover 806, insert the waste in the waste shredding unit 807, and close the cover 808. Then, the system checks if the waste receiver cover has been closed properly with a safety lock 809. If the answer is "no", then a message is generated to prompt the user to check the waste receiver cover and properly close it 810. Then, the system again checks whether the waste receiver cover has been closed properly 809. Steps 809-810 are repeated until the system determines that the waste receiver cover has been properly closed. Once the waste receiver cover has been properly closed and the answer of 809 is "yes", the system allows further actions to be performed 811.

Figure 19:
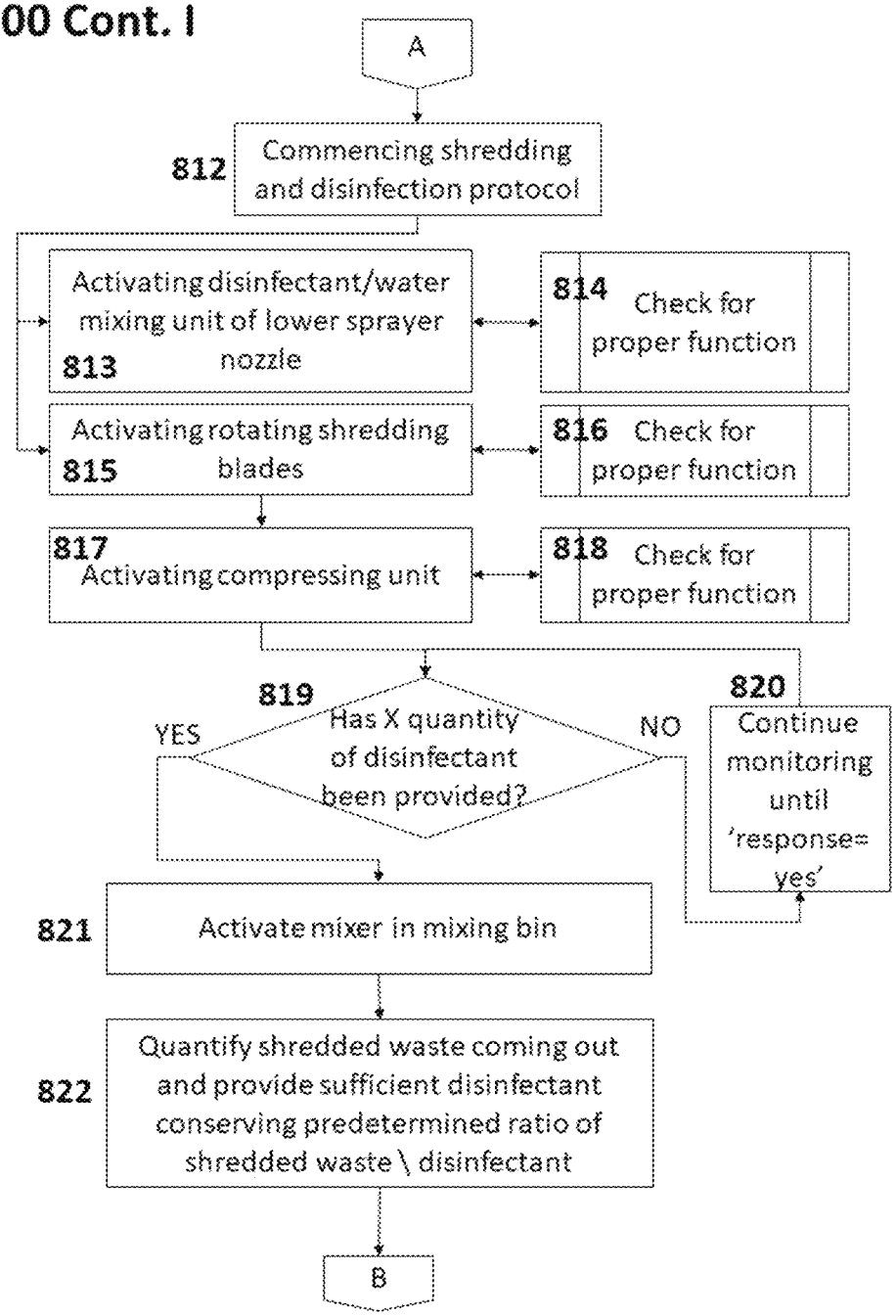

FIG. 19 shows, starting at connector "A", the continuation of the flowchart. At this point, the system starts the shredding and disinfection protocol 812. Similar to the method described above, the system begins by concurrently activating the disinfectant/water mixing unit of lower sprayer nozzle 813 and the rotating shredding blades 815. During the activation period of 813 and 815, a parallel function checks for proper function of the same 814 and 816. After a pre-determined time (typically a few seconds), the compression unit 817 is activated. Also here, a parallel function checks for proper function of the same 818. Then, the system checks if a minimum quantity of disinfectant liquid has been provided 819. This is important for the proper function of the mixing unit. If the answer is "no", then the system waits until the answer is "yes" 820. Then the system activates the mixer in the mixing unit 821. After that, the system commences to quantify the amount of shredded waste coming out the shredder and provides sufficient disinfectant according to a predetermined ratio of shredded waste to disinfectant 822.

Figure 20:
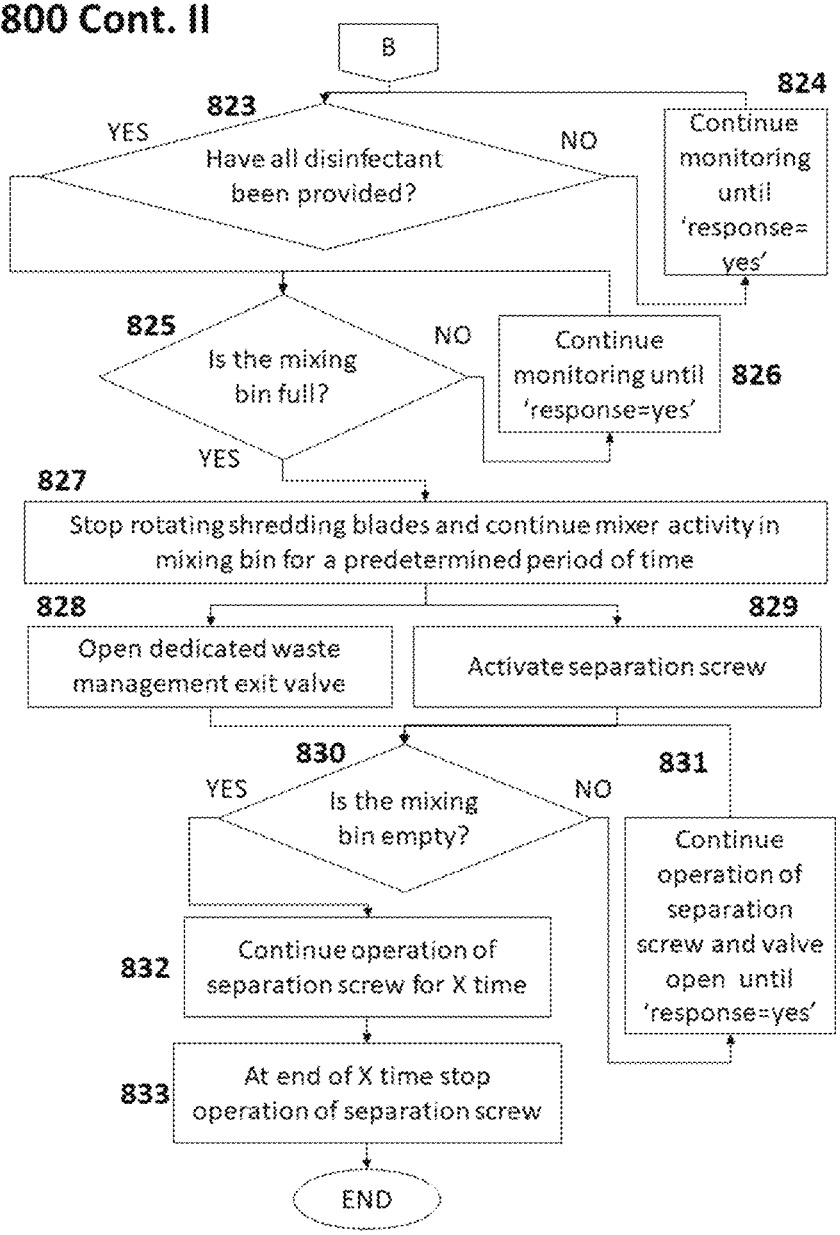

FIG. 20 shows, starting at connector "B", the continuation of the flowchart. After that, the system checks if all of the disinfectant required has been provided 823. If "no", then the system continues monitoring until the response is "yes" 824. When the answer is "yes", then the system checks if the mixing bin is at optimal capacity (about 30 liters of water and disinfectant and about 20 liters of shredded waste) 825. If "no", then the system continues monitoring until the response is "yes" 826. When the answer is "yes", the shredder stops shredding and the system activates the mixer for a pre-determined time 827. Once the mixing step is finished, the exit valve of the waste management system opens 828. Since the volume exiting the valve is regulated, the rate of evacuation of the liquid is controlled. The long screw of the separation arm is activated 829 simultaneously with the opening of the exit valve. Then the system checks if the mixing bin is empty 830. If "no", then the operation of the long screw and the opening of the valve continue until the answer is "yes" 831. When the answer is "yes", then the operation of the long screw continues for a further predetermined period of time 832 to allow the remainder of the waste to exit the separation arm. At the end of the predetermined period of time, the long screw is stopped 833. At this point the system has ended the shredding and disinfection protocol and it is ready for the next disinfection cycle.

In embodiments where there is a centrifuge at the end of the separation arm, once the long screw is activated, the centrifuge is activated as well, for a different, predetermine, period of time, as disclosed above, to provide further separation of liquid from the waste before the waste is disposed of in +the dedicated bin.

The invention claimed is:
1. A medical waste treatment system (1000), comprising:
   a. a main treatment unit (100), said main treatment unit comprising:
      i. a waste receiver cover (110); and
      ii. a waste shredding unit (120), said waste shredding unit comprising a shredding bin (121) and at least two rotating shredding blades (124);
   b. a main liquid/chemical management unit (600) which comprises:
      . a water/disinfectant mixing unit (604, 660), and
      ii. a first disinfectant delivery unit (605) interconnected to said main treatment unit (100);
   c. a separator unit (200) which comprises:
      i. a separator arm (202, 1202) comprising a long screw (201), a tray (205) and a mechanical squeezer (1205) at the distal end of said long screw (201), said tray comprising a plurality of orifices characterized by shape and diameter SD2, said shape and diameter SD2 configured to allow the passage of liquids and block passage of solids of a predefined particle shape or diameter; and
      ii. an output chute (206); and d. a plurality of motor units (300) which comprise:
   i. a shredding motor unit (301) operatively interconnected to said at least two rotating shredding blades (124);
   ii. a mixer motor unit (303) operatively interconnected to said mixing unit (132); and
   iii. a separator unit motor;
said first delivery unit (605) comprises a plurality of nozzles through which said disinfectant flows, said first delivery unit (605) being below said waste shredding unit (120);
further wherein at least one of said at least two rotating shredding blades is rotatable at different velocity from at least one other of said at least two rotating shredding blades;
wherein said main treatment unit (100) further comprises a compression unit (122) operatively interconnected to a compressing motor unit (302), said compression unit configured to push said medical waste into said shredder bin (121) towards said at least two shredding blades (124); said shredding bin has convergently shaped side walls configured for conducting a flow of said medical waste onto said at least two shredding blades (124); said compression unit comprises at least two shafts disposed at edges of said shredding bin (121) rotatable by said compressing motor unit (302); said at least two shafts each are provided with a comb secured thereto and formed by a plurality of coplanar arms being arranged in parallel to each other; said at least two shafts are reciprocally rotatable such that said coplanar arms periodically move up and down;
wherein said at least two shafts are configured to enable said medical waste to transfer to said at least two shredding blades (124) when said medical waste is pressed by said at least two combs.

2. The medical waste treatment system of claim 1, wherein said waste receiver cover further comprises a window.

3. The medical waste treatment system of claim 1, wherein said main treatment unit (100) further comprises a disinfection unit (130) which comprises a disinfectant mixing bin (131) and a mixing unit (132).

4. The medical waste treatment system of claim 1, wherein said system comprises a member of a group consisting of a mechanical squeezer 1205, a centrifuge (207) at an end of said separation arm (202) or any combination thereof.

5. The medical waste treatment system of claim 1, wherein said separator unit motor is selected from an elongated screw motor unit (304) operatively interconnected to said long screw (201), and a mechanical squeezer motor.

6. The medical waste treatment system of claim 1, wherein said waste receiver cover (110) further comprises a member of a group consisting of a UV lamp configured to disinfect user's contact area, a second disinfectant delivery unit (607) in said waste shredding unit (120) comprising a plurality of nozzles through which said disinfectant flows or any combination thereof.

7. The medical waste treatment system of claim 1, wherein said waste shredding unit (120) further comprises a grating (126), said grating comprising a plurality of orifices characterized by shape and diameter SD1, said shape and diameter configured to allow the passage of shredded medical waste in predefined particle shape and diameter.

8. The medical waste treatment system of claim 1, wherein said waste shredding unit (120) further comprises said grating (126) configured to allow the passage of shredded medical waste in predefined particle shape and diameter.

9. The medical waste treatment system of claim 1, further comprising an electrical unit (400) connectible to an operator panel unit (500).

10. The medical waste treatment system of claim 1, wherein said centrifuge (207) further comprises a UV lamp.

11. The medical waste treatment system of claim 1, wherein said system further comprises a plurality of sensors operatively interconnected to different parts of the system said sensors selected from a group consisting of:
   a. at least one waste receiver cover sensor configured to monitor if said waste receiver cover has been properly and safely closed;
   b. at least one compressing unit sensor configured to detect resistance and evaluate quantity of said waste in said waste shredding unit (120);
   c. rotating shredding blades sensors configured to monitor the current of said shredding motor unit (301);
   d. sensors of said tray and grating configured to monitor the correct positioning of said tray (205) and grating (126);
   e. at least one long screw sensor configured to monitor real-time performance information of the rotational operation of said long screw (201);
   f. at least one disinfectant RFID sensor configured to monitor a member of a group consisting of whether non-original disinfectant concentrate is present, whether the disinfectant concentrate is from a non-validated producer, the expiry date of the chemical disinfectant concentrate or any combination thereof;
   g. at least one temperature sensor;
   h. at least one flow meter and at least one pressure gauge;
   i. at least one sensor configured to measure weight of the waste;
   j. at least one sensor to determine the amount of disinfectant concentrate in the container; or
   k. any combination thereof.

12. A method to treat medical waste, comprising steps of:
   a. providing a medical waste treatment system comprising:
      i. a main treatment unit (100), said main treatment unit comprising:
         1. a waste receiver cover (110); and
         2. a waste shredding unit (120), said waste shredding unit comprising a shredding bin (121) and at least two rotating shredding blades (124);
      ii. a main liquid/chemical management unit (600) which comprises:
         1. a water/disinfectant mixing unit (604, 660), and
         2. a first disinfectant delivery unit (605) interconnected to said main treatment unit (100);
      iii. a separator unit (200) which comprises:
         1. a separator arm (202, 1202) comprising a long screw (201), a tray (205) and a mechanical squeezer (1205) at the distal end of said long screw (201), said tray comprising a plurality of orifices characterized by shape and diameter SD2, said shape and diameter SD2 configured to allow the passage of liquids and block passage of solids of a predefined particle shape or diameter; and
         2. an output chute (206); and
      iv. a plurality of motor units (300) which comprises:
         1. a shredding motor unit (301) operative interconnected to said at least two rotating shredding blades (124);

2. a mixer motor unit (303) operative interconnected to said mixing unit (132); and
3. a separator unit motor;

said first delivery unit (605) comprises a plurality of nozzles through which said disinfectant flows, said first delivery unit (605) being below said waste shredding unit (120);

at least one of said at least two rotating shredding blades is rotatable at different velocity from at least one other of said at least two rotating shredding blades;

wherein said main treatment unit (100) further comprises a compression unit (122) operatively interconnected to a compressing motor unit (302), said compression unit configured to push said medical waste into said shredder bin (121) towards said at least two shredding blades (124); said shredding bin has convergently shaped side walls configured for conducting a flow of said medical waste onto said at least two shredding blades (124); said compression unit comprises at least two shafts disposed at edges of said shredding bin (121) rotatable by said compressing motor unit (122); said at least two shafts each are provided with a comb secured thereto and formed by a plurality of coplanar arms being arranged in parallel to each other; said at least two shafts are reciprocally rotatable such that said coplanar arms periodically move up and down;

said at least two shafts are configured to enable said medical waste to transfer to said at least two shredding blades (124) when said medical waste is pressed by said at least two combs;

b. manually pressing a start button;
c. disinfecting said waste receiver cover and said waste shredding unit;
d. manually opening said waste receiver cover (110);
e. manually placing waste in said waste shredding unit (120);
f. manually closing said waste receiver cover (120);
g. automatically performing a shredding and disinfecting protocol, comprising steps of:
  i. concomitantly activating the disinfectant/water mixing unit of lower sprayer nozzle (813) and the rotating shredding blades (815);
  ii. activating the compression unit;
  iii. assessing if a minimum quantity of disinfectant has been provided (819);
  iv. activating a mixer in the mixing unit (821);
  v. quantifying the amount of shredded waste coming out the shredder and providing sufficient disinfectant according to the predetermined ratio of shredded waste/disinfectant (822);
  vi. checking if all the disinfectant required has been provided (823);
  vii. checking if the mixing bin is at optimal capacity (825);
  viii. if yes, stopping said rotating shredding blades;
  ix. activating the mixer for a predetermined period of time (827);
  x. opening the exit valve of the waste management system (828) and activating the separation arm;
  xi. activating the centrifuge at the end of the separation arm for a predetermined period of time;
  xii. checking if the mixing bin is empty (830);
  xiii. continuing operation of the separation arm for a predetermined period of time (832) to allow a remainder of said waste to exit the separation arm; and
  xiv. stopping the separation arm (833).

13. The medical waste treatment system of claim 1, further comprising a disinfection unit sensor configured to monitor the quantity of each of the contents inside said disinfectant mixing bin (131).

14. The medical waste treatment system of claim 1, wherein tearing of said waste is augmented by said at least one of said at least two rotating shredding blades being rotatable at said different velocity from said at least one other of said at least two rotating shredding blades is configured to tear waste.

15. The medical waste treatment system of claim 1, wherein correct and optimal performance of the system is controllable by software configured to control all components and sensors in said medical waste treatment system.

16. The medical waste treatment system of claim 1, wherein said software is further configured to provide traceability, said traceability selected from a group consisting of traceability of technical performance, traceability of operational efficiencies, traceability of chemical allowance, traceability of exact chemical usage according to specification or any combination thereof.

* * * * *